(12) United States Patent
Gessner et al.

(10) Patent No.: US 8,586,745 B2
(45) Date of Patent: Nov. 19, 2013

(54) SWITCHABLE SPECIAL EFFECT SUBSTANCES

(75) Inventors: Thomas Gessner, Heidelberg (DE); Ruediger Sens, Ludwigshafen (DE); Sophia Ebert, Mannheim (DE)

(73) Assignee: BASF SE, Ludwigshafen (DE)

( * ) Notice: Subject to any disclaimer, the term of this patent is extended or adjusted under 35 U.S.C. 154(b) by 118 days.

(21) Appl. No.: 12/991,710

(22) PCT Filed: May 18, 2009

(86) PCT No.: PCT/EP2009/055961
§ 371 (c)(1), (2), (4) Date: Nov. 9, 2010

(87) PCT Pub. No.: WO2009/141288
PCT Pub. Date: Nov. 26, 2009

(65) Prior Publication Data
US 2011/0060113 A1      Mar. 10, 2011

(30) Foreign Application Priority Data
May 19, 2008   (EP) .................................... 08156466

(51) Int. Cl.
*C07D 471/02*         (2006.01)
(52) U.S. Cl.
USPC ........ 546/37; 546/66; 219/121.64; 250/492.1
(58) Field of Classification Search
USPC .................. 526/259; 219/121.64; 250/492.1; 546/37, 66
See application file for complete search history.

(56) References Cited

U.S. PATENT DOCUMENTS

| 2008/0036373 A1 | 2/2008 | Itoh et al. |
| 2008/0315757 A1 | 12/2008 | McKiernan et al. |

FOREIGN PATENT DOCUMENTS

| DE | 24 29 258 | 1/1975 |
| DE | 10 2006 011269 | 9/2007 |
| DE | 10 2006 011270 | 9/2007 |
| DE | 10 2006 011271 | 9/2007 |
| WO | 98 52950 | 11/1998 |
| WO | 99 56125 | 11/1999 |
| WO | 02 077081 | 10/2002 |
| WO | 2007 071957 | 6/2007 |
| WO | 2007 099059 | 9/2007 |
| WO | 2009 040000 | 4/2009 |

OTHER PUBLICATIONS

U.S. Appl. No. 13/322,210, filed Nov. 23, 2011, Sundarraj, et al.
International Search Report issued Dec. 29, 2009 in PCT/EP09/055961 filed May 18, 2009.

*Primary Examiner* — Kriellion Sanders
(74) *Attorney, Agent, or Firm* — Oblon, Spivak, McClelland, Maier & Neustadt, L.L.P.

(57) ABSTRACT

A process for altering the absorption of electromagnetic radiation by one or more compounds of the general formulae (I)

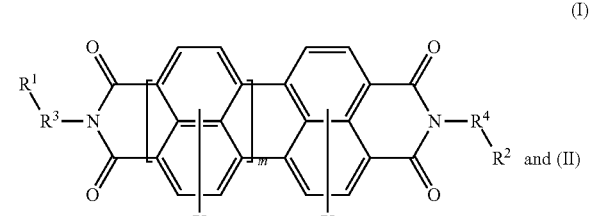

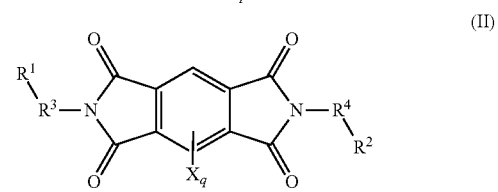

wherein these compounds are irradiated with electromagnetic radiation of wavelength from 300 to 750 nm. The use of compounds of the general formula (I) or (II) for marking materials, for example paper or mineral oil, and use of compounds of the general formula (I) or (II) for causing a color change. The use of compounds of the general formula (I) or (II) for laser welding, heat management, as a photoinitiator, as a free-radical scavenger or for detection of oxygen. A process for regulating the absorption or transmission of electromagnetic radiation by a material wherein one or more compounds of the general formula (I) or (II) are contacted with this material and these compounds are irradiated with electromagnetic radiation of wavelength from 300 to 750 nm. Specific compounds of the general formula (I).

5 Claims, No Drawings

SWITCHABLE SPECIAL EFFECT SUBSTANCES

The present invention relates to processes for altering the absorption of electromagnetic radiation by selected compounds. The invention likewise comprises the use of these compounds for detecting the marking of materials, for causing a color change, for laser welding, in heat management, or for providing free-radical scavengers or photoinitiators, and to the use for detection of oxygen. The invention further relates to processes for regulating the absorption or transmission of electromagnetic radiation by materials. Particular selected compounds and materials likewise form part of the subject matter of the invention. In addition, polymers, coatings or glasses which comprise selected compounds likewise form part of the subject matter of the present invention.

Further embodiments of the present invention can be inferred from the claims, the description and the examples. It is self-evident that the features of the inventive subject matter which have been mentioned above and those which are still to be mentioned below can be used not only in the combination specified in each case, but also in other combinations, without leaving the scope of the invention. Preferred and very preferred are especially the embodiments of the present invention in which all features have, respectively, the preferred and very preferred definitions.

It is known that perylenetetracarboxylic mono- and diimides which comprise donor radicals covalently bonded on the imide nitrogen, for example amino (Langhals et al., Chem. Eur. J. 1998, 4, 2110-2116; Mohr et al., Anal. Chem. 2000, 72, 1084-1087) or anilino (Zhang et al., J. Am. Chem. Soc. 2002, 124, 10640-10641), can exhibit a photoinduced intramolecular electron transfer and therefore have little tendency to fluoresce. Protonation of the donor radical or interaction of the donor radical with metal ions can negate the extinguishment of fluorescence. Consequently, such compounds have been proposed, for example, as pH- or metal ion-sensitive fluorescence sensors (Sauer et al., Angew. Chem. 2003, 115, 1834-1835).

Using 4-carbazol-9-ylbutane-1-sulfonic acid as a donor, an intermolecular electron transfer to N,N'-di(2-dimethylaminoethyl)-1,6,7,12-tetrachloroperylene-3,4,9,10-tetracarboximide (acceptor) in solution has been described, when the two molecules, as a result of electrostatic forces, approach one another (Bonnet et al., Synthetic Metals 156 (2006) 1292-1298).

O'Neil et al. (Science 257 (1992) 63-65) describe N,N'-diphenyl-3,4,9,10-perylenebis(dicarboximides) which bear porphyrin substituents on the phenyl groups. After the absorption of laser pulses having a wavelength of 585 nm, a transient absorption is observed at 713 nm and a further absorption at 546 nm. An absorption in the infrared is not described. The lifetime of the transient absorption is in the region of a few 100s of picoseconds.

Patent applications DE 10 2006 011 269 A1, DE 10 2006 011 270 A1 and DE 10 2006 011 271 A1 disclose free-radical anions which are obtainable by reduction of perylene dyes, perylene-3,4:9,10-tetracarboximides. The free-radical anions and salts thereof are used as colorants, among other uses.

None of the prior art documents cited above discloses a long-lasting and controllable alteration in the absorption of electromagnetic radiation by molecules in conjunction with excitation by electromagnetic radiation.

In order to regulate the absorption of electromagnetic radiation, for example the IR absorption of materials, compounds which absorb in the IR (WO 02/077081) are frequently added to the materials. According to the application or profile of requirements, these compounds are added to the materials in different concentrations. This imparts permanent IR absorption to these materials. However, this IR absorption is generally not switchable.

For the visible and invisible marking of materials, substances which absorb or fluoresce in the visible spectral region and in the IR are frequently used (WO 98/52950, WO 99/56125, WO 2007/099059). However, the marking of these materials is permanent and cannot simply be switched off and on without removing the markers.

It was therefore an object of the present invention to provide compounds whose absorption in the visible or IR wavelength range is not permanent but rather switchable. It was a further object of the present invention to discover substances whose regulable (switchable) absorption permits use of these substances as markers of materials. It was another objective of the invention to provide simple processes which enable regulation of the absorption of electromagnetic radiation by materials.

These and other objects, as is evident from the disclosure content of the present invention, are achieved by the different embodiments of the process according to the invention for altering the absorption of electromagnetic radiation by means of chemical compounds or materials which comprise chemical compounds which are described below.

The invention therefore provides a process for altering the absorption of electromagnetic radiation by means of one or more compounds of the general formulae (I)

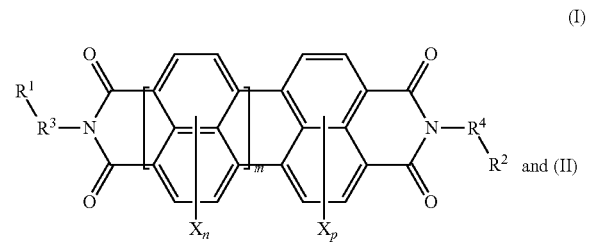

and (II)

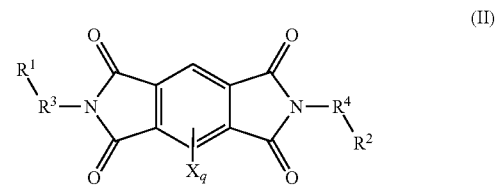

wherein these compounds are irradiated with electromagnetic radiation of wavelength from 300 to 750 nm and where the symbols and indices are each defined as follows $R^1$, $R^2$ are the same or different and are each independently amino, $C_1$-$C_8$-alkylamino, $C_1$-$C_8$-dialkylamino, arylamino, diarylamino, N-heterocyclyl, triarylaminyl, hydroxyl, $C_1$-$C_8$-alkoxy, aryloxy, $R^3$, $R^4$ are the same or different and are each independently a single bond, $C_1$-$C_8$-alkylene, $C_3$-$C_6$-cycloalkylene, arylene, $C_8$-$C_{14}$-phenylalkylene, X are the same or different and are each independently $C_1$-$C_{20}$-alkoxy, $C_1$-$C_{20}$-alkylthio, aryloxy, arylthio, halogen, cyano, $CO_2R$, $SO_3R$, $SO_2R$, or a group

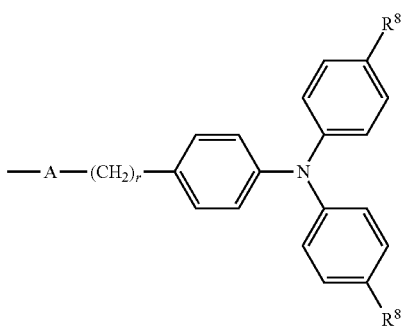

where
A is S, $SO_2$,
r is 2, 3, 4, 5, 6,
$R^8$ is $C_1$-$C_{20}$-alkyl, $C_1$-$C_{20}$-alkoxy,
and
if m=1, different X together may be a thio group,
R are the same or different and are each independently H, $C_1$-$C_8$-alkyl, aryl,
n, p is 0, 1, 2, 3 or 4,
m is 0, 1, 2 or 3,
q is 0, 1 or 2,
and where
the substituents R, $R^1$, $R^2$, $R^3$ or $R^4$ may each be interrupted at any position by one or more heteroatoms with valences saturated if appropriate by hydrogen, where the number of these heteroatoms is not more than 4, preferably not more than 3, even more preferably not more than 2 and especially not more than 1, and/or may be substituted in each case at any position, but not more than five times, preferably not more than four times and more preferably not more than three times, by $NR^5R^6$, $CONR^5R^6$, COOM, $COOR^5$, $SO_3M$, $SO_3R^5$, where
$R^5$, $R^6$ are the same or different and are each independently H, $C_1$-$C_8$-alkyl, aryl,
M is H, alkali metal, $NR^7_4$,
$R^7$ is independently H, $C_1$-$C_8$-alkyl,
CN, $NO_2$, $C_1$-$C_{20}$-alkyl, $C_1$-$C_{20}$-alkoxy, aryl, aryloxy, heterocycles, heteroatoms or halogen, where these may likewise be substituted not more than twice, preferably not more than once, by the groups mentioned.

In the context of this invention, expressions of the $C_a$-$C_b$ form denote chemical compounds or substituents with a particular number of carbon atoms. The number of carbon atoms can be selected from the entire range from a to b, including a and b; a is at least 1 and b is always greater than a. The chemical compounds or the substituents are specified further by expressions of the $C_a$-$C_b$-V form. V here represents a chemical compound class or substituent class, for example alkyl compounds or alkyl substituents.

In the context of the present invention, infrared radiation (IR radiation for short) refers to electromagnetic waves in the spectral region between visible light and the longer-wavelength microwaves. This corresponds to a wavelength range from about 780 nm to 1 mm. In the case of short-wave IR radiation (from 760 nm), reference is often made to near infrared (NIR), and at wavelengths of approx. 5-25 micrometers to mid infrared (MIR). Extremely long-wave IR radiation (25 μm-1 mm) is referred to as far infrared (FIR). Infrared radiation forms part of thermal radiation.

In the context of the present invention, visible light refers to electromagnetic waves in the spectral region from about 380 nm to 780 nm.

In the context of the present invention, substances which absorb electromagnetic radiation in the wavelength range of IR radiation are also referred to as IR absorbers. IR absorbers preferably have an absorption in the wavelength range from 760 to 2000 nm, very preferably from 780 to 1500 nm, and an extinction coefficient for IR radiation of at least 100 l/(cm*mol). The extinction coefficient for IR radiation is preferably more than 1000 l/(cm*mol) and very preferably more than $10^4$ l/(cm*mol).

In the context of the present invention, substances which absorb visible light are also referred to as colored. Colored substances preferably have extinction coefficients for visible light of at least 100 l/(cm*mol). The extinction coefficient for visible light is preferably more than 1000 l/(cm*mol) and very preferably more than $10^4$ l/(cm*mol).

Halogen represents fluorine, chlorine, bromine or iodine, preferably fluorine, chlorine or bromine, more preferably chlorine or bromine.

Specifically, the collective terms specified for the different substituents are defined as follows:

$C_1$-$C_{20}$-Alkyl: straight-chain or branched hydrocarbon radicals having up to 20 carbon atoms, for example $C_1$-$C_{10}$-alkyl or $C_{11}$-$C_{20}$-alkyl, preferably $C_1$-$C_8$-alkyl, for example $C_1$-$C_3$-alkyl such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_8$-alkyl such as heptyl, octyl, 2-ethylhexyl, 2,4,4-trimethylpentyl, 1,1,3,3-tetramethylbutyl.

Aryl: a mono- to tricyclic aromatic ring system comprising from 6 to 14 carbon ring members, for example phenyl, naphthyl or anthracenyl, preferably a mono- to bicyclic ring system, more preferably a monocyclic aromatic ring system.

Aryloxy is a mono- to tricyclic aromatic ring system (as specified above) which is attached via an oxygen atom (—O—), preferably a mono- to bicyclic ring system, more preferably a monocyclic aromatic ring system.

Arylthio is a mono- to tricyclic aromatic ring system (as specified above) which is attached via an oxygen atom (—S—), preferably a mono- to bicyclic ring system, more preferably a monocyclic aromatic ring system.

$C_1$-$C_8$-Alkylene: straight-chain or branched hydrocarbon radicals having from 1 to 8 carbon atoms, for example $C_1$-$C_6$-alkylene, especially methylene, dimethylene, trimethylene, tetramethylene, pentamethylene or hexamethylene.

$C_8$-$C_{14}$-Phenylalkylene: straight-chain or branched hydrocarbon radicals having from 8 to 14 carbon atoms, where the alkylene chain is interrupted by a phenylene group or comprises a terminal phenylene group, preferably $C_9$-$C_{10}$-phenylalkylene.

Heterocycles: five- to twelve-membered, preferably five- to nine-membered, more preferably five- to six-membered ring systems comprising oxygen, nitrogen and/or sulfur atoms and optionally a plurality of rings, such as furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

N-Heterocyclyl: heterocycle attached via a nitrogen atom, preferably pyrrolidino, piperidino N'-alkylpiperazinyl, morpholino, pyrrolyl, indolyl, carbazolyl, phenothiazinyl, very preferably pyrrolidino, piperidino, morpholino, carbazolyl.

$C_1$-$C_{20}$-Alkoxy is a straight-chain or branched alkyl group having from 1 to 20 carbon atoms (as specified above) which is attached via an oxygen atom (—O—), for example $C_1$-$C_{10}$-alkoxy or $C_{11}$-$C_{20}$-alkoxy, preferably $C_1$-$C_8$-alkyloxy, especially preferably $C_1$-$C_3$-alkoxy, for example methoxy, ethoxy, propoxy.

$C_1$-$C_{20}$-Alkylthio is a straight-chain or branched alkyl group having from 1 to 20 carbon atoms (as specified above) which is attached an oxygen atom (—S—), for example $C_1$-$C_{10}$-alkylthio or $C_{11}$-$C_{20}$-alkylthio, preferably $C_1$-$C_8$-alkylthio, especially preferably $C_1$-$C_3$-alkylthio.

Heteroatoms are preferably oxygen, nitrogen, sulfur or phosphorus.

Triarylaminyl is preferably N,N-diarylanilin-4-yl.

$C_1$-$C_8$-Dialkylamino is an amino group having two alkyl substituents, where each of the alkyl substituents, independently of the other, may have 1 to 8 carbon atoms. The two alkyl substituents are preferably the same.

For the performance of the process according to the invention, it is of course likewise possible to use mixtures of the compounds of the general formula (I) or mixtures of the compounds of the general formula (II) or else mixtures of the compounds of the general formula (I) and (II).

The symbols of the general formulae (I) or (II) are preferably each defined as follows:
$R^1$, $R^2$ are the same or different and are each independently amino, $C_1$-$C_8$-alkylamino, $C_1$-$C_8$-dialkylamino, arylamino, diarylamino, N,N-diarylanilin-4-yl, carbazolyl,
$R^3$, $R^4$ are the same or different and are each independently a single bond, $C_1$-$C_8$-alkylene,
X are the same or different and are each independently $C_1$-$C_{20}$-alkoxy, aryloxy, halogen, cyano, $SO_2R$, or a group

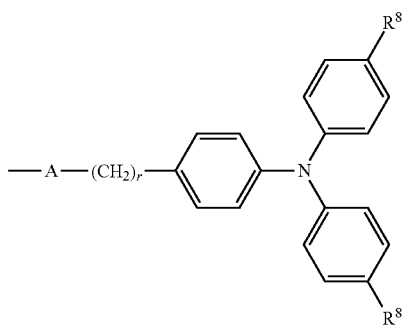

where
A is S, $SO_2$,
r is 2, 3, 4, 5, 6,
$R^8$ is $C_1$-$C_{20}$-alkyl, $C_1$-$C_{20}$-alkoxy,
m is 1 or 2,
where the substituents $R^1$, $R^2$, $R^3$ and $R^4$ may each be substituted at any position as mentioned above or interrupted by heteroatoms, and all other symbols and indices are each as defined at the outset. The substituents $R^1$, and $R^2$ here are more preferably substituted by $C_1$-$C_{20}$-alkyl or $C_1$-$C_{20}$-alkoxy groups.

More preferably, the symbols of the general formulae (I) or (II) are each defined as follows:
$R^1$, $R^2$ are both amino, $C_1$-$C_8$-alkylamino, $C_1$-$C_8$-dialkylamino, arylamino, diarylamino, N,N-diarylanilin-4-yl, carbazolyl,
$R^3$, $R^4$ are the same or different and are each independently $C_1$-$C_8$-alkylene,
X are the same or different and are each independently halogen, cyano, alkoxy, or a group

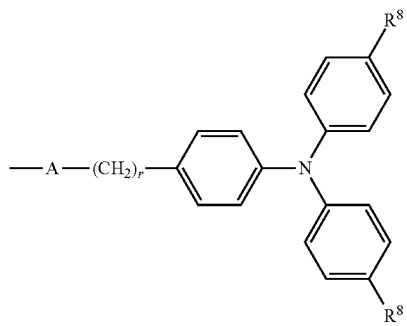

where
A is S, $SO_2$,
r is 2, 3, 4, 5, 6,
$R^8$ is $C_1$-$C_{20}$-alkyl, $C_1$-$C_{20}$-alkoxy,
n, p are 0, 1 or 2,
m 1 or 2,
where the substituents $R^1$, $R^2$, $R^3$ and $R^4$ may each be substituted at any position as mentioned above or interrupted by heteroatoms, and all other symbols and indices are each as defined at the outset. The substituents $R^1$ and $R^2$ here are more preferably substituted by $C_1$-$C_{20}$-alkyl or $C_1$-$C_{20}$-alkoxy groups.

General processes for preparing the compounds of the general formulae (I) or (II) are known to those skilled in the art, for example, from F. Würthner, Chem. Commun. 2004, p. 1564-1579. For example, the compounds of the general formulae (I) or (II) can be obtained by reacting perylenebis (dicarboxylic anhydrides) or peryleneimide-dicarboxylic anhydride with amines in a solvent at generally 80-160° C., with addition, for example in the case of reactions with arylamines, of Lewis acids, for example zinc acetate.

According to the invention, the alteration in the absorption of electromagnetic radiation by irradiation of compounds of the general formula (I) or (II) is performed with electromagnetic radiation of wavelength from 300 to 750 nm. Preference is given to irradiating in a wavelength range from 400 to 700 nm. One possible explanation for the alteration in the absorption is that the irradiation forms altered compounds, for example free-radical anions of the compounds of the general formula (I) or (II). These altered compounds which form through the above-described irradiation from the compounds of the general formula (I) or (II) are referred to in the context of the present invention as "compounds altered by the irradiation" or as "compounds with altered absorption of electromagnetic radiation".

The irradiation is effected, for example, with a white light source, preferably by means of solar radiation, or likewise preferably with a xenon lamp. The irradiation can likewise be effected by means of narrowband electromagnetic radiation, preferably with the aid of lasers or laser diodes.

The compounds of the general formulae (I) or (II) or materials which are in contact with these compounds can, depending, for example, on the end use, be irradiated once, over repeating intervals or else continuously. The irradiation time, unless continuous irradiation is effected, is typically in the range from milliseconds to hours. Frequently, irradiation times in the range from a few seconds up to one hour are used. The irradiation intensity is frequently of minor significance; it merely has to be ensured that the duration and the intensity achieve an altered absorption sufficient for the particular use. A higher irradiation intensity generally shortens the irradiation time needed for this purpose. Too high an irradiation intensity can, however, lead to destruction of the compounds of the general formulae (I) or (II). The person skilled in the art is capable of using routine tests to determine suitable irradiation intensities and times for the particular compound.

The alteration in the absorption of electromagnetic radiation which is caused by the process according to the invention means that the irradiation causes altered compounds to have absorption bands for electromagnetic radiation in regions of the electromagnetic spectrum which were not present before the irradiation. These alterations in the absorption properties preferably bring about a visible color change. The process according to the invention preferably effects a bathochromic shift in the absorption spectrum, which means that the compounds altered by irradiation are capable of absorbing electromagnetic radiation with greater wavelength than the compounds of the general formula (I) or (II) before the irradiation. For example, this preferably results in a visually perceptible color shift with these compounds, more particularly including from a colorless to a colored impression. In addition, the irradiation preferably causes an absorption in the IR range which had not been present beforehand, which means that the compounds altered by irradiation are IR absorbers.

In general, the compounds of the general formula (I) or (II), after being irradiated once, exhibit the altered absorption of electromagnetic radiation, depending on the molecular structure and/or environmental effects, for a period following the irradiation of from a few milliseconds to days. The altered absorption is preferably maintained for a period in the range from a few seconds to several hours.

The alterations in the absorption caused by the irradiation can generally disappear again as described above, but are frequently maintained for a period of several hours or days.

The exclusion of oxygenous gases, especially of air, prolongs the lifetime of the alterations caused in the absorption of electromagnetic radiation. Conversely, with the aid of this effect, the presence of oxygen can be detected, i.e. irradiation allows the compounds of the general formula (I) or (II) to be used as oxygen probes or indicators. In the presence of oxygen, the lifetime of the alterations caused in the absorption is frequently shortened significantly. The determination of the shortening of the lifetime allows the content of oxygen to be determined. The invention therefore further provides for the use of compounds of the general formula (I) or (II), on completion of irradiation, for the detection of oxygen.

In addition, compounds of the general formula (I) or (II), after the inventive irradiation, find use as free-radical scavengers, with the advantage that the use as free-radical scavengers is switchable in a controlled manner by irradiation.

In addition, compounds of the general formula (I) or (II), after the inventive irradiation, find use as photoinitiators, for example for polymerization reactions.

The above-described processes according to the invention also find use in all fields of industry in which it is useful, through irradiation of compounds of the general formula (I) or (II), to obtain compounds whose absorption properties with respect to electromagnetic radiation are altered. This alteration in properties can frequently be exploited as a switch. A material which is in contact with the compounds of the general formula (I) or (II) frequently likewise has new properties imparted to it as a result of this alteration in properties. The amount of compounds of the general formula (I) or (II) which are contacted with a material, more particularly are added to the material, depends on the details of the particular use and can vary over a wide range.

In a preferred embodiment, the compounds of the general formulae (I) or (II) are dissolved in a solvent and irradiated, in order to be used preferably as IR absorbers or to cause a color change. Suitable solvents include, for example, organic solvents, for example toluene, xylene, NMP, DMF, dimethylacetamide, pyridine, dichloromethane, tetrahydrofuran and ethyl acetate. Preference is given to using NMP, pyridine, DMF or dimethylacetamide. It will be appreciated that it is also possible to use mixtures of solvents.

The lifetime of the usability in accordance with the invention of IR absorbers or of the provision of a color change of the compounds of the general formulae (I) and (II) depends on the particular structure of the molecule and, if appropriate, on the kind of material with which the compound is in contact. The lifetime of usability varies generally, on completion of irradiation, within the range from a few milliseconds to hours; frequently, the lifetime of usability is in the range from a few seconds to several hours.

When the compounds of the general formulae (I) or (II) or the materials which are in contact with these compounds are irradiated continuously or over repeating intervals, continuous usability as an IR absorber or continuous provision of a color change can be achieved.

The present invention further provides a process for regulation, especially switchable regulation, of the absorption of electromagnetic radiation by a material, which comprises contacting one or more compounds of the general formulae (I) or (II) with this material and irradiating these compounds with electromagnetic radiation of wavelength from 300 to 750 nm. Preference is given to adding the compounds of the general formula (I) or (II) to the material, i.e. they are present in the material, more particularly in homogeneous distribution. The compounds of the general formula (I) or (II) are likewise preferably present essentially at the surface of the material, for example in the form of a layer comprising the compounds of the general formula (I) or (II), more particularly in the form of a coating layer.

The amount of compounds of the general formula (I) or (II) is generally from 0.001 to 6.0 $g/m^2$, based on the surface area of the material which is irradiated. Preference is given to using from 0.03 to 3.0 $g/m^2$, more preferably from 0.05 to 2.5 $g/m^2$ and especially from 0.09 to 1.0 $g/m^2$.

The compounds are generally used in amounts of from 0.02 ppm to 10000 ppm, based on the weight of the material. The compounds are used preferably in an amount of from 1 ppm to 5000 ppm, preferentially from 2 ppm to 3000 ppm, especially from 5 ppm to 2000 ppm.

In the process according to the invention, the material is preferably a window, for example a glass window or a plastic window. The process according to the invention can be applied to all types of window, for example in buildings, motor vehicles, aircraft or other machines.

With the aid of the process according to the invention, preference is given to regulating the absorption of electromagnetic radiation by a material in the IR wavelength range.

In general, by virtue of the process according to the invention for regulating the IR absorption of a material, at least 5% of the incident IR radiation is absorbed, preferably at least 10%, more preferably at least 20% and especially at least 50%. In a specific embodiment, more than 80% of the incident IR radiation is absorbed, more particularly more than 90%.

In a specific embodiment of the process according to the invention for regulating IR absorption, the compounds of the general formula (I) or (II) are present at the surface of a window. The solar radiation irradiates the compounds of the general formula (I) or (II) as described above, resulting in regulation of the IR absorption at the surface of a window.

In a further specific embodiment of the process according to the invention for regulating IR absorption, the compounds of the general formula (I) or (II) are present incorporated within a window material. The solar radiation irradiates the compounds of the general formula (I) or (II) as described above, resulting in regulation of the IR absorption of the window.

Additionally preferably, with the aid of the process according to the invention, the absorption of electromagnetic radiation by a material is regulated in the wavelength range of visible light.

In a specific embodiment of the process according to the invention for regulating the absorption of visible light, the compounds of the general formula (I) or (II) are present at the surface of a window. The solar radiation irradiates the compounds of the general formula (I) or (II) as described above, resulting in regulation of the absorption of visible light at the surface of a window. More particularly, this results in tinting of the window.

In a further specific embodiment of the process according to the invention for regulating the absorption of visible light, the compounds of the general formula (I) or (II) are present incorporated within a window material. The solar radiation irradiates the compounds of the general formula (I) or (II) as described above, resulting in regulation of the absorption of visible light in the window. More particularly, this results in tinting of the window.

The invention further provides a process for regulating the transmission of electromagnetic radiation, preferably in the IR or in the wavelength range of visible light, by a material, especially by a window, this material being in contact with compounds of the general formula (I) or (II). After the above-described irradiation, these compounds function as absorbers, especially for IR radiation or visible light, and therefore reduce the transmission of the particular radiation by the material.

More particularly, the transmission of the infrared fraction of solar radiation through a window can be regulated, and hence the heating of a room behind the window by the solar radiation can be delayed or reduced (heat management).

In addition, the processes according to the invention or the compounds altered by the irradiation can therefore be used in heat management or for thermal insulation.

The invention therefore provides a process for heat management or for thermal insulation, wherein the materials are first contacted with compounds of the general formulae (I) or (II). To alter the IR absorption of materials and hence for the heat management, an increase in the absorption in the IR is brought about in the material by the above-described processes according to the invention.

The compounds of the general formulae (I) or (II) are preferably present in contact with windows, especially windowpanes. The process according to the invention regulates the IR transmission through the window and hence enables heat management of the room behind the window. In this context, the windows may of course, as well as windows in buildings, of course also be windows of automobiles, aircraft or machines with drivers' cabs.

In addition, the transmission of the visible fraction of solar radiation by a window can preferably be regulated and hence the brightness of a room behind the window can be regulated in the event of incidence of sunlight (brightness management).

In addition, the inventive compounds can therefore be used in brightness management analogously to the manner in which they are used for heat management as described above.

The present invention further provides for the exploitation of the process according to the invention for the marking of materials. Preference is given to using the process according to the invention in the detection of the marking of paper, mineral oil, plastics or metal surfaces. Particular preference is given to using the compounds of the general formula (I) or (II) as markers for mineral oils or paper. Very preferred is the use for marking paper, more particularly as a security feature for documents, securities or banknotes.

One advantage of the use as a marker for mineral oils is that mineral oils frequently, in the spectral region of the absorption which is altered after irradiation of the compounds (I) or (II), themselves have no absorption, and an excellent signal/noise ratio is achieved for the detection even of ultrasmall amounts of the marker. This is especially true for an alteration in the absorption in the IR obtained with the aid of the process according to the invention.

Frequently, the compounds of the general formulae (I) or (II) themselves absorb visible light and can therefore also be used for the staining of materials, especially of paper and plastics. This staining can be reduced or removed by the process according to the invention, under the condition that the absorption spectrum of the compound altered by irradiation has experienced a bathochromic shift into the IR region.

The invention further provides a process for marking materials, wherein the materials are contacted with compounds of the general formulae (I) or (II). To detect the marking, alterations in the absorption are generated and detected in the material by the above-described processes according to the invention. The detection is generally effected visually (with the naked eye) or with the aid of an (absorption) spectrometer.

The inventive marking of paper is effected, for example, by the application of compounds of the general formulae (I) and/or (II) to the surface of the paper to be marked, for example by spraying, impregnating with or dropwise application of solutions comprising the compounds of the formulae (I) or (II). More particularly, the compounds of the general formulae (I) and (II) can be applied to the paper in a mixture with a printing ink. The amount of compounds of the general formulae (I) and (II) may vary within a wide range according to the application. Preference is given to using less than 10% by weight of compounds of the general formulae (I) or (II) based on the amount of printing ink, very preferably less than 5% by weight. The marking can be detected, for example, visually by a color change or with the aid of an (absorption) spectrometer.

Mineral oil is marked in accordance with the invention by adding compounds of the general formulae (I) or (II) to the mineral oil to be marked. The amount of compounds of the general formulae (I) and (II) can vary within a wide range according to the application. Preference is given to using less than 5 ppm of compounds of the general formulae (I) or (II) based on the amount of mineral oil used, very preferably less than 1 ppm. The detection of the marking can be undertaken, for example, with the aid of an (absorption) spectrometer.

In addition, the processes according to the invention can be used in laser welding.

The invention therefore further provides a process for laser welding of materials, wherein the materials are first contacted with compounds of the general formulae (I) or (II). For the welding, an increase in the IR absorption is brought about in the material by the above-described processes according to the invention.

The welding of materials, especially of plastics, is effected by absorption of laser energy in or on the plastics material by the laser-sensitive IR absorbers added, which lead to local heating of the material by absorbing the laser energy. In the laser welding of, for example, two materials, significant heating is generated by absorption of the laser energy in the joint region of the materials to be welded, such that the materials melt and the two materials fuse to one another. Frequently, it is sufficient when only one of the materials comprises laser-sensitive IR absorbers in the material or as a layer on the surface. The laser weldability depends on the nature of the materials, especially plastics, and on the wavelength and the radiative power of the laser used. For example, $CO_2$ lasers, excimer lasers or Nd:YAG lasers are useful for laser welding for the process according to the invention.

In general, the total content of compounds of the general formulae (I) and (II) is between 0.0001 and 1% by weight, based on the material to be welded. The content is preferably from 0.001 to 0.1% by weight. More particularly, sufficient weldability of plastics arises within this range from 0.001 to 0.1% by weight.

The compounds of the general formulae (I) and (II) can be incorporated into virtually all plastics with the aid of processes known to those skilled in the art, for example by extrusion, especially in order to impart laser weldability to them. Typical plastics materials are those in which the plastics matrix is based on poly(meth)acrylate, polyamide, polyurethane, polyolefins, styrene polymers and styrene copolymers, polycarbonate, silicones, polyimides, polysulfone, polyethersulfone, polyketones, polyetherketones, PEEK, polyphenylene sulfide, polyesters (such as PET, PEN, PBT), polyethylene oxide, polyurethane, polyolefins, cycloolefin copolymers or fluorinated polymers (such as PVDF, EFEP, PTFE). Likewise possible is incorporation into blends which include abovementioned plastics as components, or in polymers which are derived from these classes and have been altered by subsequent reactions. These materials are known in a wide variety and are commercially available.

The invention further provides novel specific compounds of the general formula (I) as described at the outset, where
$R^1$, $R^2$ are the same or different and are each independently $C_1$-$C_8$-alkylamino, $C_1$-$C_8$-dialkylamino, arylamino, diarylamino, triarylaminyl, carbazolyl
$R^3$, $R^4$ are the same or different and are each independently $C_1$-$C_8$-alkylene, arylene,
X are the same or different and are each independently halogen, cyano, or a group

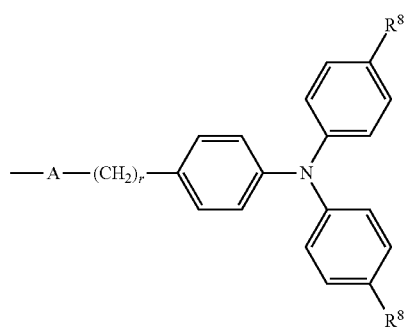

where
A is S, $SO_2$,
r is 2, 3, 4, 5, 6,
$R^8$ is $C_1$-$C_{20}$-alkyl, $C_1$-$C_{20}$-alkoxy,
n, p are 0, 1 or 2,
m is 0 or 1, and where the substituents $R^1$, $R^2$ may each be substituted at any position, but not more than five times, by $C_1$-$C_{20}$-alkyl, $C_1$-$C_{20}$-alkoxy, and the compounds which have been obtained from these compounds by irradiation with the aid of electromagnetic radiation of wavelength from 300 nm to 750 nm and have been altered by irradiation.

Preference is given to specific compounds of the general formula (I) as described at the outset, where
$R^1$, $R^2$ are the same or different and are each independently

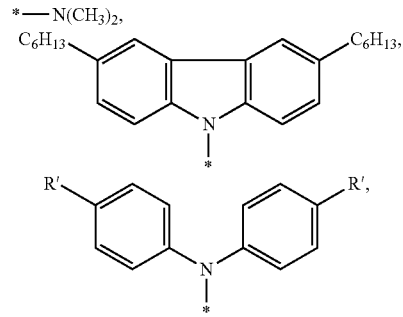

$R^3$, $R^4$ are the same or different and are each independently
*—$CH_2$—$CH_2$—*, *—$CH_2$—$CH_2$—$CH_2$—*,

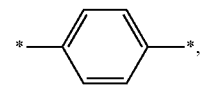

X are the same or different and are each independently halogen, cyano, or a group

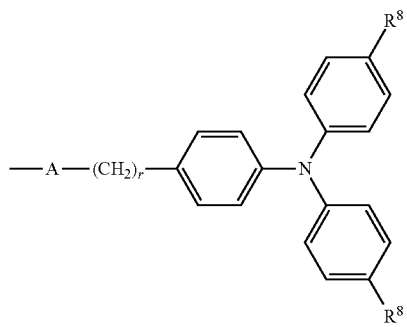

where
A is S, $SO_2$,
r is 2, 3, 4, 5, 6,
$R^8$ is $C_1$-$C_{20}$-alkyl, $C_1$-$C_{20}$-alkoxy,
n, p are each 0, 1 or 2,
m is 0 or 1,
R' is H, $C_6$-$C_8$-alkyl, $C_6$-$C_8$-alkoxy,
and where "*" denotes the site of attachment of the chemical bond, and the compounds which have been obtained from these compounds by irradiation with the aid of electromagnetic radiation of wavelength from 300 nm to 750 nm and have been altered by irradiation. R' is preferably H or

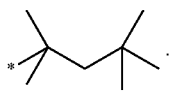

Very preferably, the substituents $R^1=R^2$ and $R^3=R^4$, and all substituents X are the same as one another.

Very particularly preferred novel and inventive specific compounds of the general formula (I) as described at the outset are specified in the examples together with novel and inventive intermediates for preparing them.

The invention further provides novel intermediates of the general formulae (III), (IV) and (V), which can find use in the preparation of the compounds of the general formulae (I) and (II):

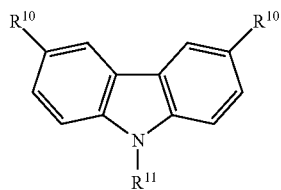

where
$R^{10}$ is $C_1$-$C_{20}$-alkyl, $C_1$-$C_{20}$-alkoxy,
$R^{11}$ is —$(CH_2)_r$—OH,

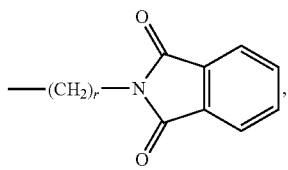

—$(CH_2)_r$—$NH_2$,
—$(CH_2)_r$—$COOR^{22}$,
—$(CH_2)_r$—$NH_3^+Y^-$,
—$(CH_2)_r$—SH,
where r=2, 3, 4, 5 or 6 and $Y^-$=singly negatively charged anion equivalent as a counterion, for example $Cl^-$, $Br^-$, $½SO_4^{2-}$, preferably halide; $R^{22}$ is $C_1$-$C_{20}$-alkyl, preferably methyl or ethyl.

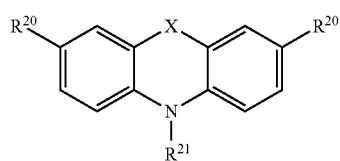

where
$R^{20}$ is $C_1$-$C_{20}$-alkyl, $C_1$-$C_{20}$-alkoxy,
$R^{21}$ is H, —$(CH_2)_r$—OH,

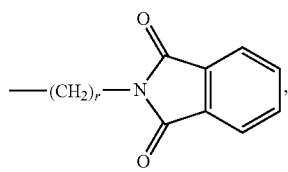

—$(CH_2)_r$—$NH_2$,
—$(CH_2)_r$—$NH_3^+Y^-$,
—$(CH_2)_r$—SH,
where r=2, 3, 4, 5 or 6 and $Y^-$=singly negatively charged anion equivalent as a counterion, for example $Cl^-$, $Br^-$, $½SO_4^{2-}$, preferably halide,
X is 2H, S;

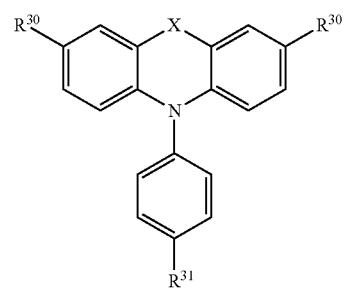

where
$R^{30}$ is $C_1$-$C_{20}$-alkyl, $C_1$-$C_{20}$-alkoxy,
$R^{31}$ is H, CHO, $CH_2CN$, CH=CH—CN, CH=CH—$COOR^{32}$, $(CH_2)_r$—$NH_2$, $(CH_2)_r$—$COOR^{32}$, $NH_2$, $NO_2$, halogen, $(CH_2)_r$—SH, $(CH_2)_r$—NHCO-t-Bu where r=2, 3, 4, 5 or 6,
X is a single bond, 2H, S,
$R^{32}$ is $C_1$-$C_{20}$-alkyl,
with the proviso that $R^{30}$ is not $C_1$-$C_4$-alkyl or $C_1$-$C_4$-alkoxy and,
at the same time, $R^{31}$ is not H or CHO and, at the same time, X is not 2H.

In the formulae above, 2H mean two individual hydrogen atoms which are each attached individually to the two rings in formula (IV) or (V).

The invention further provides materials, for example glass, plastic, textiles or metals which are in contact with the above-described novel specific compounds of the general formula (I), and especially comprise them.

For the contacting, especially the incorporation, of compounds of the general formulae (I) and (II), it is possible to use the methods for contacting materials with other additives which are known to those skilled in the art for the particular material. In the case of paper, these are, for example, bulk dyeing with dyes or the application of printing inks. In the case of plastics, the processes for coating plastics or the processes for bulk dyeing of plastics, for example with the aid of an extruder, can be used. The techniques of spin-coating or of vapor deposition of substances onto materials can also be used here.

In addition, it is possible first to dissolve the compounds of the general formulae (I) and (II) in a solvent, to contact the materials with the solution and then to remove the solvent, for example by a drying process.

The invention therefore further provides polymers, coatings or glasses comprising compounds of the general formula (I) or (II).

The present invention allows the use of compounds in applications in which a desired absorption in the IR or in the visible region of the spectrum should not be permanent but rather switchable. In addition, the invention provides processes for reliable marking of materials. The invention likewise provides simple processes which enable the absorption of electromagnetic radiation by materials to be regulated.

The examples which follow are intended to illustrate the invention, but without limiting it.

EXAMPLES

Example 1

Preparation of N,N'-bis[2-(3,6-dihexyl-N-carbazolyl) ethyl]-perylenetetracarboximide a)
N-Methoxycarbonylmethyl-3,6-di-n-hexylcarbazole

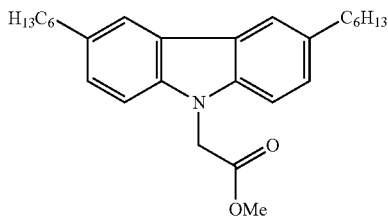

α) A solution of 10.07 g (30.0 mmol) of 3,6-di-n-hexylcarbazole (preparation according to J. J. Piet et al., Chem. Phys. Lett. 289 (1998) 13-18) in 50 ml of anhydrous dimethylformamide was admixed under nitrogen with 11.2 g (81.0 mmol) of potassium carbonate and heated to 50° C. After stirring for 45 min, 14.19 g (90.0 mmol) of 97% methyl bromoacetate were added dropwise within 1 hour. Subsequently, the reaction mixture was stirred at 50° C. for 24 hours. The reaction mixture was poured onto 300 ml of water and extracted with 300 ml of xylene. The aqueous phase was removed and extracted three times by shaking with 200 ml each time of xylene. The combined organic phases were washed twice with 200 ml each time of water and once with saturated sodium chloride solution, dried over sodium sulfate and then concentrated to dryness. 13.72 g of crude product were obtained, which were purified on silica gel (60 Å, 60-200 μm) with toluene/n-heptane (2:1) as the eluent. 8.03 g (66% of theory) of pale yellow oil were obtained.

$^1$H NMR analysis:

$^1$H NMR (CDCl$_3$, 400 MHz): δ=7.88 (s; 2H, arom. H), 7.27 (d; 2H, arom. H), 7.20 (d; 2H, arom. H), 4.96 (s; 2H, N—CH$_2$—), 3.69 (s; 3H, O—CH$_3$), 2.77 (t; 4H, Ph-CH$_2$—), 1.69 (mc; 4H, —CH$_2$—), 1.25-1.42 (m; 12H, —CH$_2$—), 0.88 ppm (t; 6H, —CH$_3$)

β) A solution of 3.00 g (8.94 mmol) of 3,6-di-n-hexylcarbazole and 1.55 g (9.84 mmol) of 97% methyl bromoacetate in 40 ml of methyl isobutyl ketone were stirred with 7.15 g of 50% NaOH and 0.14 g of Aliquat 175 at room temperature for 30 min. Subsequently, the reaction solution was admixed with 70 ml of water. The aqueous phase was removed, and extracted by shaking with 30 ml of methyl isobutyl ketone and then with 20 ml of ethyl acetate. The combined organic phases were washed twice with 50 ml each time of saturated sodium chloride solution, dried over magnesium sulfate and concentrated to dryness. 3.6 g (94% of theory) of yellowish oil were obtained. According to $^1$H NMR, the compound is identical to example 1aα).

b) N-(2-Hydroxyethyl)-3,6-di-n-hexylcarbazole

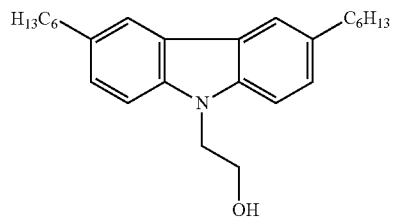

To a suspension, cooled to 0° C., of 0.88 g (22.4 mmol) of 97% lithium aluminum hydride in 30 ml of tetrahydrofuran (THF) was added dropwise, under argon, a solution of 8.00 g (19.6 mmol) of N-methoxycarbonylmethyl-3,6-di-n-hexylcarbazole in 30 ml of THF within 15 min, in the course of which the temperature was kept at 0-5° C. The reaction mixture was allowed to warm to room temperature and stirred for a further 30 min. After the dropwise addition of 20 ml water/THF, the solution was stirred at room temperature for 15 min and then admixed with 2 ml of 10% NaOH, which precipitated a solid which was filtered off. The filtrate was admixed with 200 ml of diethyl ether/water (1:1). The aqueous phase was removed and extracted by shaking twice with 100 ml each time of diethyl ether. The combined organic phases were twice washed to neutrality with 100 ml of water each time and with 100 ml of saturated sodium chloride solution, dried over sodium sulfate and concentrated to dryness. 7.5 g (100% of theory) of colorless solid were obtained.

$^1$H NMR analysis:

$^1$H NMR (CDCl$_3$, 400 MHz): δ=7.87 (s; 2H, arom. H), 7.33 (d; 2H, arom. H), 7.25 (d; 2H, arom. H), 4.41 (t; 2H, N—CH$_2$—CH$_2$—), 4.00 (t; 2H, N—CH$_2$—CH$_2$—), 2.77 (t; 4H, Ph-CH$_2$—), 1.70 (mc; 4H, —CH$_2$—), 1.23-1.42 (m; 12H, —CH$_2$—), 0.83 ppm (t; 6H, —CH$_3$)

c)
N-[2-(N-Phthalimido)ethyl]-3,6-di-n-hexylcarbazole

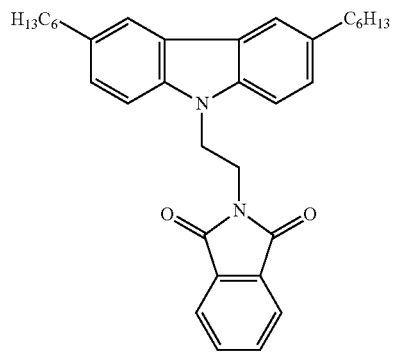

To a solution of 7.50 g (19.8 mmol) of N-(2-hydroxyethyl)-3,6-di-n-hexylcarbazole, 3.14 g (21.3 mmol) of phthalimide and 5.29 g (20.0 mmol) of 99% triphenylphosphine in 200 ml of THF were added dropwise, under nitrogen, 3.94 g (22.1 mmol) of 98% diethyl azodicarboxylate (DEAD) at room temperature (exothermic). After stirring at room temperature for 27 hours, the reaction mixture was to concentrated to dryness and then admixed with ice-cold methanol. The solid was filtered off with suction. 8.93 g (89% of theory) of yellow solid were obtained, which melted at 118-119° C.

$^1$H NMR analysis:

$^1$H NMR (CDCl$_3$, 400 MHz): δ=7.84 (s; 2H, arom. H), 7.79 (mc; 2H, arom. H), 7.69 (mc; 2H, arom. H), 7.39 (d; 2H, arom. H), 7.23 (d; 2H, arom. H), 4.52 (t; 2H, N—CH$_2$—), 4.08 (t; 2H, N—CH$_2$—), 2.75 (t; 4H, Ph-CH$_2$—), 1.67 (mc; 4H, —CH$_2$—), 1.23-1.42 (m; 12H, —CH$_2$—), 0.88 ppm (t; 6H, —CH$_3$)

d) N-(2-Aminoethyl)-3,6-di-n-hexylcarbazole

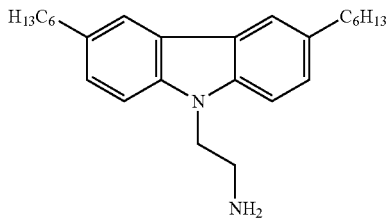

A solution of 8.90 g (17.5 mmol) of N-[2-(N-phthalimido) ethyl]-3,6-di-n-hexylcarbazole in 150 ml of THF and 150 ml of ethanol were admixed with 1.79 g (35.0 mmol) of 98% hydrazine monohydrate and then the mixture was heated to boiling under reflux for 20 hours. After 80 ml of water had been added, the reaction mixture was concentrated, then admixed with 160 ml each of water and diethyl ether and adjusted to pH 13.6 with 20% NaOH. The aqueous phase was removed and extracted twice with 150 ml each time of diethyl ether. The combined organic phases were washed twice with 150 ml each time of water and dried over sodium sulfate. After the filtrate had been concentrated, 5.25 g (79% of theory) of yellow-brown oil were isolated, which crystallized after a while and melted at 56° C.

$^1$H NMR analysis:

$^1$H NMR (CDCl$_3$, 400 MHz): δ=7.88 (s; 2H, arom. H), 7.33 (d; 2H, arom. H), 7.26 (d; 2H, arom. H), 4.34 (t; 2H, N—CH$_2$—), 3.19 (t; 2H, —CH$_2$—NH$_2$), 2.77 (t; 4H, Ph-CH$_2$—), 1.70 (mc; 4H, —CH$_2$—), 1.23-1.43 (m; 12H, —CH$_2$—), 0.88 ppm (t; 6H, —CH$_3$)

e) N,N'-Bis[2-(3,6-dihexyl-N-carbazolyl)ethyl] perylenetetracarboximide

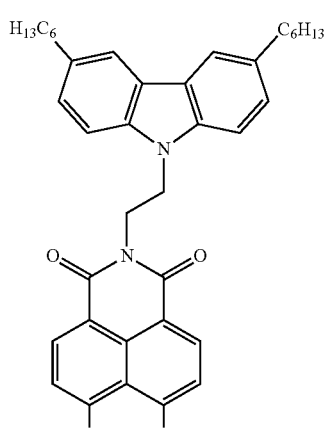

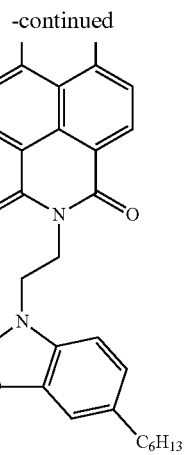

2.00 g (5.10 mmol) of perylenetetracarboxylic dianhydride and 4.05 g (10.7 mmol) of N-(2-aminoethyl)-3,6-di-n-hexylcarbazole were stirred at 120° C. in 100 ml of N-methylpyrrolidinone (NMP) for 6 hours. After cooling to room temperature, 100 ml of methanol were added. The precipitated solid was filtered off with suction and dried (5.53 g). The crude product was recrystallized in 270 ml of chlorobenzene. The solid was filtered off with suction, washed with chlorobenzene and pentane, and dried. 4.65 g (82% of theory) of red microcrystals with an m.p. of 314-315° C. were obtained.

UV/Vis (chloroform): λ$_{max}$ (ε)=526 nm (84730)

C$_{76}$H$_{80}$N$_4$O$_4$ (M=1113.49 g/mol):

| | | | | | | | | | |
|---|---|---|---|---|---|---|---|---|---|
| calc. | C | 81.98 | H | 7.24 | N | 5.03 | O | 5.75 |
| found | C | 81.8 | H | 7.2 | N | 4.9 | O | 5.7 |

Example 2

Preparation of N,N'-Bis[3-(3,6-di-n-hexyl-N-carbazolyl)propyl]perylenetetracarboximide a) N-[3-(N-Phthalimido)propyl]-3,6-di-n-hexylcarbazole

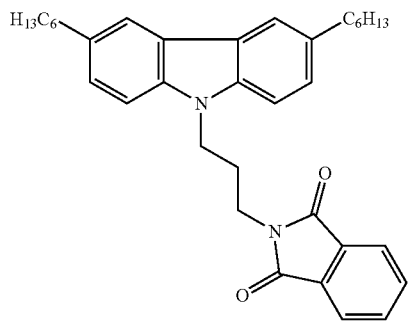

To a suspension of 1.28 g (32.0 mmol) of 60% sodium hydride in mineral oil in 25 ml of anhydrous THF was added dropwise a solution of 6.71 g (20.0 mmol) of 3,6-di-n-hexyl-carbazole in 25 ml of anhydrous THF within 15 min. After the dropwise addition of a solution of 8.76 g (32.0 mmol) of 98% N-(3-bromopropyl)phthalimide in 25 ml of anhydrous THF within 15 min, the reaction mixture was heated to boiling under reflux for 21 hours. After cooling to room temperature, 10 ml of THF/water (1:1) were added dropwise, in order to destroy excess sodium hydride. The reaction mixture was admixed with 300 ml of water and with 50 ml of saturated sodium chloride solution, and extracted with 300 ml of xylene. The aqueous phase was removed and extracted by shaking twice with 200 ml of xylene each time. The combined organic phases were washed twice with 200 ml of water each time and once with 200 ml of saturated sodium chloride solution, dried over sodium sulfate, and after filtration, concentrated to dryness. The crude product (12.46 g of yellow oil) was purified on silica gel (60 Å, 60-200 μm) with n-heptane/ethyl acetate (10:1) as the eluent. 7.52 g (72% of theory) of dark yellow oil were obtained.

b) N-(3-Aminopropyl)-3,6-di-n-hexylcarbazole

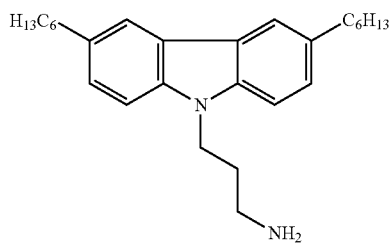

A solution of 6.91 g (13.2 mmol) of N-[3-(N-phthalimido)propyl]-3,6-di-n-hexylcarbazole in 100 ml of THF and 100 ml of ethanol was admixed with 1.35 g (26.4 mmol) of 98% hydrazine monohydrate and then heated to boiling under reflux for 20.5 hours. After 120 ml of water had been added, the reaction mixture was concentrated, then admixed with 120 ml of water and 100 ml of diethyl ether and adjusted to pH 13.5 with 20% NaOH. The aqueous phase was removed and extracted twice with 120 ml each time of diethyl ether. The combined organic phases were washed twice with 100 ml each time of water and dried over sodium sulfate. After the filtrate had been concentrated, 4.24 g (82% of theory) of pale yellow oil were isolated, which crystallized after a while.

$^1$H NMR analysis:

$^1$H NMR (CDCl$_3$, 400 MHz): δ=7.85 (s; 2H, arom. H), 7.18-7.32 (m; 4H, arom. H), 4.29 (t; 2H, N—CH$_2$—), 2.77 (t; 4H, Ph-CH$_2$—), 2.67 (t; 2H, —CH$_2$—NH$_2$), 1.95 (q; 2H, —CH$_2$—CH$_2$—NH$_2$), 1.70 (mc; 4H, —CH$_2$—), 1.23-1.43 (m; 12H, —CH$_2$—), 0.88 ppm (t; 6H, —CH$_3$)

c) N,N'-Bis[3-(3,6-di-n-hexyl-N-carbazolyl)propyl] perylenetetracarboximide

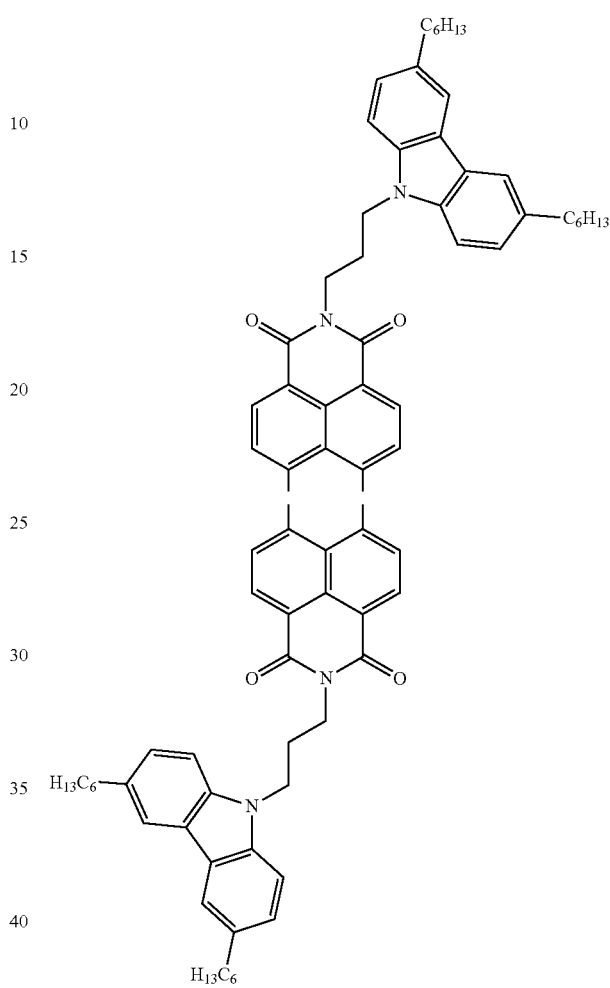

4.20 g (10.7 mmol) of N-(3-aminopropyl)-3,6-di-n-hexylcarbazole and 2.00 g (5.10 mmol) of perylenetetracarboxylic dianhydride were heated to 120° C. with stirring in 50 ml of N-methylpyrrolidinone (NMP) and kept at this temperature for 8.5 hours. After the reaction mixture had been cooled to room temperature, 150 ml of methanol were added, which precipitated a solid. This was filtered off with suction, washed twice with methanol and dried. 5.64 g of crude product were purified by means of flash chromatography on silica gel (60 Å, 60-200 μm) with methylene chloride/n-heptane/acetone (10:3:1) as the eluent. 4.50 g (78% of theory) of dark red solid with an m.p. of 218-220° C. were obtained.

UV/Vis (methylene chloride): λ$_{max}$ (ε)=524 nm (73040)

C$_{78}$H$_{84}$N$_4$O$_4$ (M=1141.56 g/mol):

| | | | | | | | | |
|---|---|---|---|---|---|---|---|---|
| calc. | C | 82.07 | H | 7.42 | N | 4.91 | O | 5.61 |
| found | C | 82.0 | H | 7.4 | N | 4.8 | O | 5.8 |

Example 3

Preparation of N,N'-bis(3-dimethylaminopropyl)-1,6,7,12-tetrachloroperylenetetracarboximide

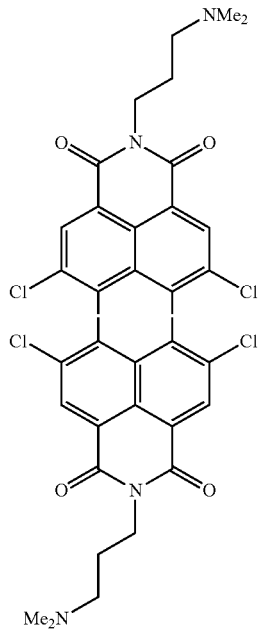 [SMILES: CN(C)CCCN1C(=O)c2cc(Cl)c3c4c(Cl)cc5c6c(cc(Cl)c(c7c(Cl)cc(c2c37)C1=O)c64)C(=O)N(CCCN(C)C)C5=O]

5.30 g (10.0 mmol) of 1,6,7,12-tetrachloroperylenetetracarboxylic dianhydride and 2.45 g (24.0 mmol) of N,N-dimethyl-1,3-propylenediamine were heated to 80° C. in 100 ml of NMP with stirring and under nitrogen, and kept at this temperature for 4 hours. After the reaction mixture had been cooled to room temperature, it was filtered. The residue was washed with methanol and dried. The crude product (3.21 g) was recrystallized twice from o-dichlorobenzene. 1.09 g (16% of theory) of orange solid were obtained, which decomposed from 246° C.

UV/Vis (methylene chloride): $\lambda_{max}$ ($\epsilon$)=518 nm (39990)
$C_{34}H_{28}Cl_4N_4O_4$ (M=698.44 g/mol):

| calc. | C | 58.47 | H | 4.04 | Cl | 20.30 | N | 8.02 | O | 9.16 |
|---|---|---|---|---|---|---|---|---|---|---|
| found | C | 58.1 | H | 4.1 | Cl | 20.7 | N | 8.0 | | |

Example 4

Preparation of N,N'-bis[2-(3,6-dihexyl-N-carbazolyl)ethyl]-1,6,7,12-tetrachloroperylenetetracarboximide

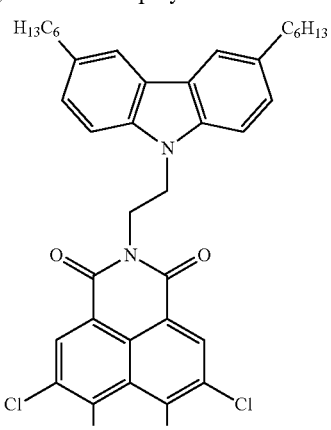

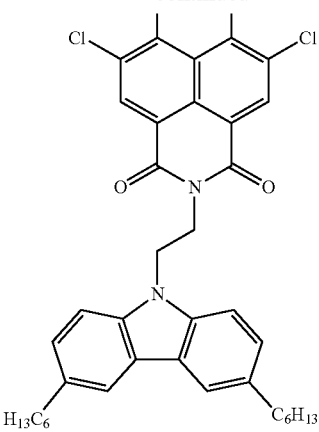

The preparation was effected correspondingly to that in example 1 with 2.00 g (3.77 mmol) of 1,6,7,12-tetrachloroperylenetetracarboxylic dianhydride. 1.37 g (29% of theory) of dark brown-red solid having an m.p. of 277° C. were obtained.

UV/Vis (methylene chloride): $\lambda_{max}$ ($\epsilon$)=520 nm (39620)
$C_{76}H_{76}Cl_4N_4O_4$ (M=1251.29 g/mol):

| calc. | C | 72.95 | H | 6.12 | Cl | 11.33 | N | 4.48 | O | 5.11 |
|---|---|---|---|---|---|---|---|---|---|---|
| found | C | 73.3 | H | 6.3 | Cl | 11.4 | N | 3.8 | O | 4.9 |

Example 5

Preparation of N,N'-bis[3-(3,6-di-n-hexyl-N-carbazolyl)propyl]-1,6,7,12-tetrachloroperylenetetracarboximide

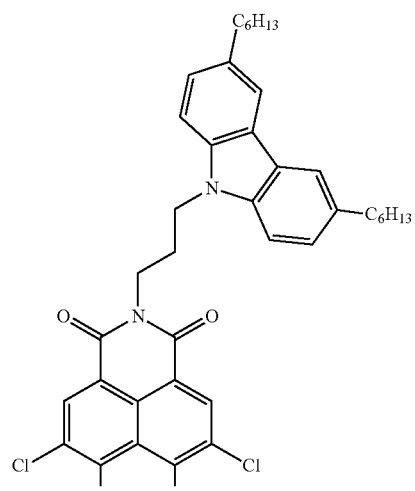

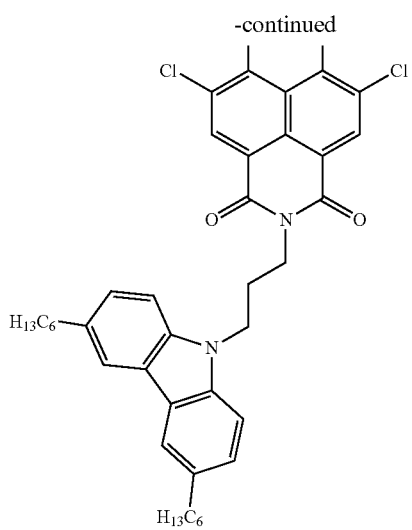

The preparation was effected correspondingly to that in example 2 with 2.50 g (4.72 mmol) of 1,6,7,12-tetrachloroperylenetetracarboxylic dianhydride. 2.54 g (56% of theory) of red-brown solid were obtained, which sintered together at 107° C.

UV/Vis (methylene chloride): $\lambda_{max}$ ($\epsilon$)=518 nm (37610)

$C_{78}H_{80}Cl_4N_4O_4$ (M=1279.34 g/mol):

| calc. | C | 73.23 | H | 6.30 | Cl | 11.08 | N | 4.38 | O | 5.00 |
|---|---|---|---|---|---|---|---|---|---|---|
| found | C | 72.9 | H | 6.5 | Cl | 11.1 | N | 4.3 | O | 5.2 |

Example 6

Preparation of N,N'-Bis[4-(N,N-diphenylamino)phenyl]-1,6,7,12-tetrachloroperylenetetracarboximide

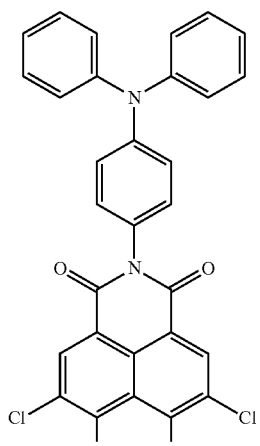

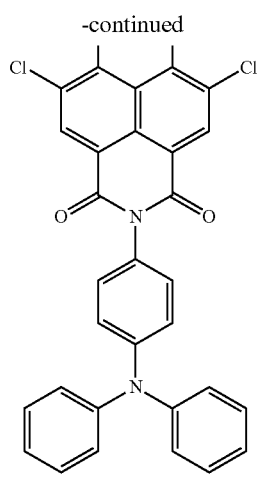

3.18 g (6.00 mmol) of 1,6,7,12-tetrachloroperylenetetracarboxylic dianhydride, 3.90 g (15.0 mmol) of N,N-diphenyl-p-phenylenediamine and 0.15 g (0.075 mmol) of zinc acetate were added to 60 ml of chlorobenzene and the mixture was heated to boiling under reflux for 8 hours. After cooling to room temperature, the precipitate was filtered off with suction, washed with methanol and dried (3.50 g). The crude product was dissolved in a relatively large amount of chlorobenzene while heating. The solution was hot-filtered. The filtrate was concentrated and blanketed with diethyl ether at room temperature. After standing in a refrigerator for three days, the crystallized solid was filtered off with suction, washed and dried. 0.55 g (9% of theory) of red-brown solid having an m.p. of >410° C. were obtained.

UV/Vis (methylene chloride): $\lambda_{max}$=518 nm

MALDI-TOF-MS: m/e=1012.3 (calc. 1012.1)

Example 7

Preparation of N,N'-bis{-4-[N,N-bis(1,1,3,3-tetramethylbutyl-4-phenyl)-amino]phenyl]-1,6,7,12-tetrachloroperylenetetracarboximide

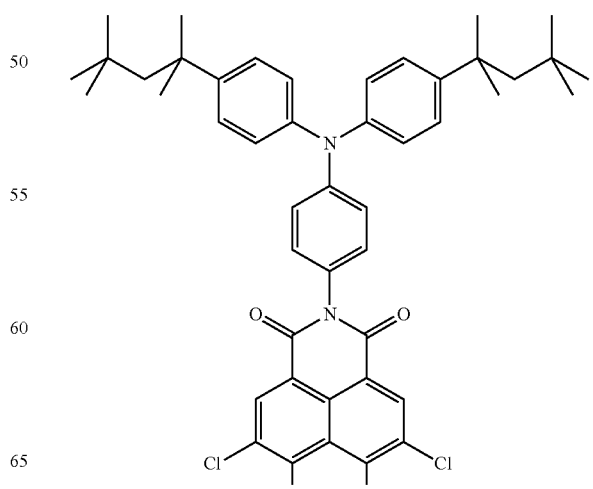

25

-continued

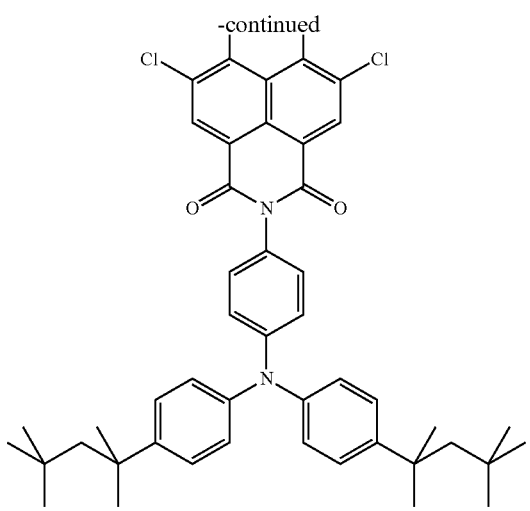

3.18 g (6.00 mmol) of 1,6,7,12-tetrachloroperylenetetracarboxylic dianhydride, 7.27 g (15.0 mmol) of N,N-bis[4-(1,1,3,3-tetramethylbutyl)phenyl]-p-phenylenediamine and 0.15 g (0.075 mmol) of zinc acetate were added to 60 ml of chlorobenzene and heated to boiling under reflux for 5 hours. After cooling to room temperature, the precipitate was filtered off with suction, washed with methanol and dried (8.05 g). The crude product was purified by chromatography on silica gel (60 Å, 60-200 μm) with toluene/n-heptane (3.5:1 to 2:1). 2.05 g (54% of theory) of pink solid having an m.p. of 374-375° C. were obtained.

UV/Vis (methylene chloride): $\lambda_{max}$ ($\epsilon$)=520 nm (48910)
$C_{92}H_{96}Cl_4N_4O_4$ (M=1463.63 g/mol):

| calc. | C | 75.45 | H | 6.47 | Cl | 9.79 | N | 3.87 | O | 4.42 |
|-------|---|-------|---|------|----|----|---|------|---|------|
| found | C | 75.7  | H | 6.8  | Cl | 9.3  | N | 3.8  |   |      |

Example 8

Preparation of N,N'-bis[3-(3,6-di-n-hexyl-N-carbazolyl)propyl]-1,7-dibromoperylenetetracarboximide

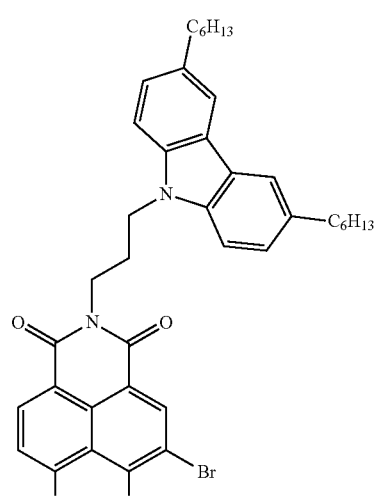

26

-continued

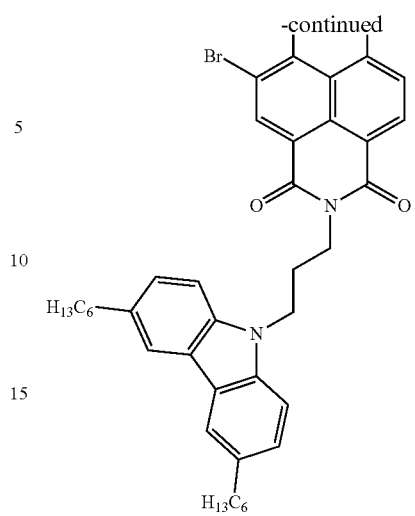

6.00 g (10.9 mmol) of dibromoperylenetetracarboxylic dianhydride and 9.00 g (22.9 mmol) of N-(3-aminopropyl)-3,6-dihexylcarbazole were dissolved in 100 ml of chlorobenzene. The solution was heated to 80° C. and kept at this temperature for 5.5 hours. After cooling to room temperature, the solution was concentrated to dryness and then admixed with 70 ml of methanol. After stirring for three hours, the solid was filtered off with suction, washed with methanol and dried (13.0 g). The crude product was purified on silica gel (60 Å, 60-200 μm) with methylene chloride as the eluent. 9.2 g (65% of theory) of red solid were obtained. According to $^1$H NMR, the substance comprised 18% of the isomeric N,N'-bis[3-(3,6-di-n-hexyl-N-carbazolyl)propyl]-1,6-dibromoperylenetetracarboximide.

UV/Vis (methylene chloride): $\lambda_{max}$ ($\epsilon$)=526 nm (48440)
$C_{78}H_{82}Br_2N_4O_4$ (M=1299.36 g/mol):

| calc. | C | 72.10 | H | 6.36 | Br | 12.30 | N | 4.31 | O | 4.93 |
|-------|---|-------|---|------|----|-------|---|------|---|------|
| found | C | 72.0  | H | 6.5  | Br | 12.4  | N | 4.3  | O | 5.0  |

Example 9

Preparation of N,N'-bis{4-[N,N-bis(1,1,3,3-tetramethylbutyl-4-phenyl)-amino]phenyl}-1,7-dibromoperylenetetracarboximide

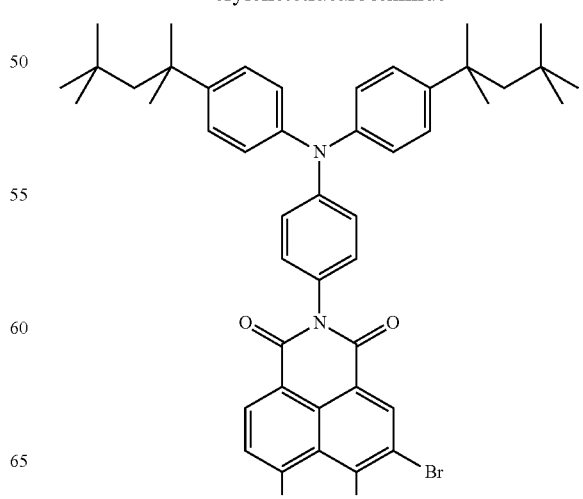

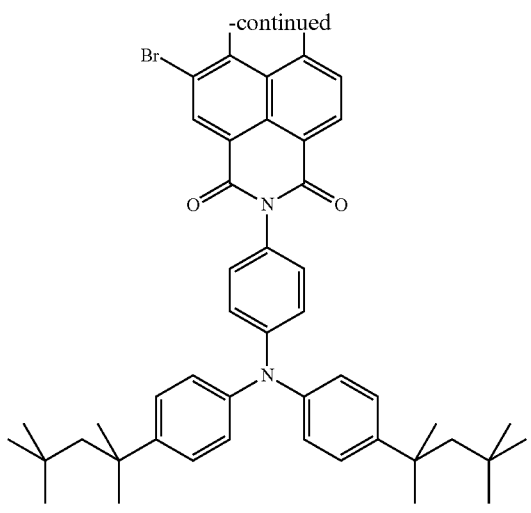

The preparation was effected correspondingly to that in example 7 with 3.30 g (6.0 mmol) of dibromoperylenetetracarboxylic dianhydride instead of 1,6,7,12-tetrachloroperylenetetracarboxylic dianhydride. 2.08 g (23% of theory) of red-brown solid were obtained. According to $^1$H NMR, the substance comprised small amounts of the 1,6-dibromo isomer.

UV/Vis (methylene chloride): $\lambda_{max}$ ($\epsilon$)=526 nm (605101 $C_{92}H_{98}Br_2N_4O_4$ (M=1483.64 g/mol):

| calc. | C | 74.48 | H | 6.66 | Br | 10.77 | N | 3.78 | O | 4.31 |
|---|---|---|---|---|---|---|---|---|---|---|
| found | C | 74.5 | H | 6.8 | Br | 11.4 | N | 3.7 | O | 4.0 |

Example 10

Preparation of N,N'-bis{3-[4-(N,N-di-n-hexylphenylamino)phenyl]propyl}-1,6,7,12-tetrachloroperylenetetracarboximide a) N,N-(Di-4-n-hexylphenyl)aniline

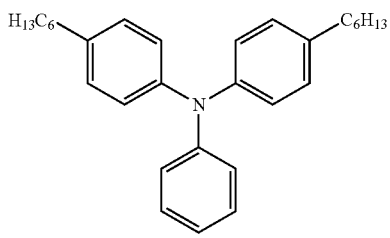

A mixture of 203 g (0.845 mol) of 4-bromo-n-hexylbenzene (prepared according to M. P. Aldred et al., J. Mater. Chem. 2005, 15, 3208-3213), 30.2 g (0.325 mol) of aniline, 105 g (1.09 mol) of sodium tert-butoxide, 11 g (0.012 mol) of tris(dibenzylidene-acetone)dipalladium and 8.4 g (0.015 mol) of 1,1'-bis(diphenylphosphino)ferrocene in 1000 ml of toluene was heated to 90° C. and kept at this temperature for 16 hours. After cooling to room temperature, methylene chloride was added. The mixture was filtered. The filtrate was concentrated to dryness. The residue was taken up in methylene chloride and purified by chromatography on silica gel with petroleum ether as the eluent. 120 g (90% of theory) of the triarylamine were obtained.

$^1$H NMR analysis:
$^1$H NMR (400 MHz, CDCl$_3$): δ=7.20 (mc, 2H, arom. H), 7.00 (mc; 11H, arom. H), 2.55 (t; 4H, Ph-CH$_2$—), 1.60 (mc; 4H, Ph-CH$_2$—CH$_2$—), 1.27-1.37 (m; 12H, —CH$_2$—), 0.83-0.91 ppm (t; 6H, —CH$_3$).

b) 4-[N,N-(Di-4-n-hexylphenyl)amino]benzaldehyde

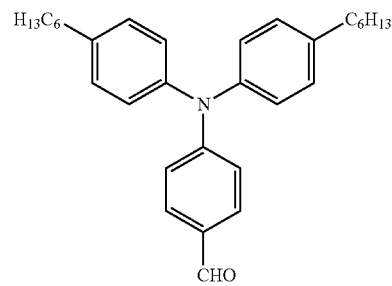

To a solution of 234 g (0.567 mol) of N,N-(di-4-n-hexylphenyl)aniline in 940 ml of DMF were added dropwise 181 g (1.19 mol) phosphorus oxychloride at 0° C. Subsequently, the reaction mixture was heated to 95° C. and stirred at this temperature for 24 hours. The reaction mixture was poured into ice-water, neutralized with NaOH and extracted with methylene chloride. The organic phase was removed, washed with water and dried over sodium sulfate. The crude product obtained after concentration to dryness was purified by chromatography on silica gel. 170 g (67% of theory) of the desired aldehyde were obtained.

$^1$H NMR analysis:
$^1$H NMR (400 MHz, CDCl$_3$): δ=9.77 (s; 1H, CHO), 7.64 (mc; 2H, arom. H), 7.14 (mc; 4H, arom. H), 7.08 (mc; 4H, arom. H), 6.94 (mc; 2H, arom. H), 2.59 (t; 4H, Ph-CH$_2$—), 1.62 (m; 4H, Ph-CH$_2$—CH$_2$—), 1.31-1.35 (m; 12H, —CH$_2$—), 0.89 ppm (t; 6H, —CH$_3$).

c) 4-[N,N-(Di-4-n-hexylphenyl)amino]cinnamonitrile

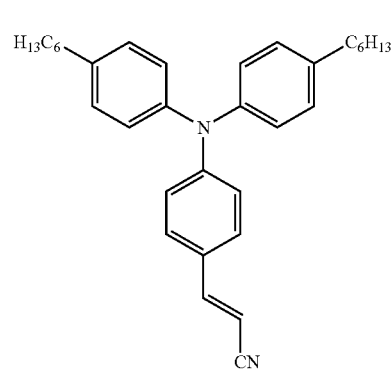

To a solution of 73.5 g (0.415 mol) of dimethyl cyanomethanephosphonate in 2500 ml of anhydrous THF were added 170 ml (2.5 mol/l) of n-butyllithium at −78° C. under nitrogen. After stirring at −78° C. for 2 hours, a solution of 170.6 g (0.386 mol) of 4-[N,N-(di-4-n-hexylphenyl)amino]

benzaldehyde in 1200 ml of anhydrous THF was added. Subsequently, the reaction mixture was allowed to come to room temperature with stirring within 3 hours. 1000 ml of water were added. The mixture was extracted with ethyl acetate. The combined organic phases were dried, filtered and concentrated to dryness. The crude product was purified by chromatography on silica gel. 172 g (96% of theory) of the desired nitrile were obtained.

$^1$H NMR analysis:

$^1$H NMR (400 MHz, CDCl$_3$): δ=7.22-7.25 (m; 3H, arom. H, =CH-Ph), 7.09-7.11 (m; 4H, arom. H), 7.02-7.04 (m; 4H, arom. H), 6.91 (d; 2H, arom. H), 5.62 (d; 1H, NC—CH=), 2.57 (t; 4H, Ph-CH$_2$—), 1.59-1.62 (m; 4H, Ph-CH$_2$—C$\underline{H}_2$—), 1.32-1.36 (m; 12H, —CH$_2$—), 0.87 ppm (t; 6H, —CH$_3$).

d) 4-(3-Aminopropyl)-N,N-di-(4-n-hexylphenyl)aniline

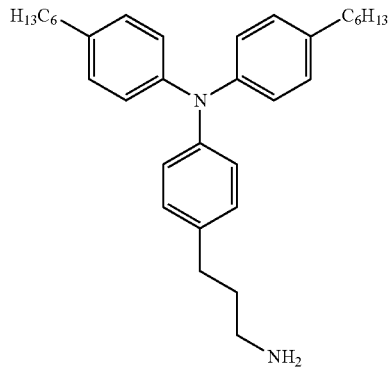

A solution of 47 g (0.195 mol) of 4-[N,N-(di-4-n-hexylphenyl)amino]cinnamonitrile in 2000 ml of n-propanol was heated to boiling under reflux for 30 min. Subsequently, 120 g (5.2 mol) of sodium were added in portions. The reaction mixture was stirred for one hour and then cooled to room temperature. 500 ml of water were added. The reaction mixture was extracted with ethyl acetate. The organic phase was dried, filtered and concentrated to dryness. The crude product was purified by chromatography on silica gel. 43.7 g (92% of theory) of amine were obtained.

$^1$H NMR analysis:

$^1$H NMR (400 MHz, CDCl$_3$): δ=7.01-7.03 (m; 6H, arom. H), 6.95-6.97 (m; 6H, arom. H), 2.74 (t; 2H, —CH$_2$—NH$_2$), 2.59 (mc; 2H, —C$\underline{H}_2$—CH$_2$—CH$_2$—NH$_2$), 2.53 (mc; 4H, Ph-CH$_2$—), 1.77 (mc; 2H, —CH$_2$—C$\underline{H}_2$—CH$_2$—NH$_2$), 1.57-1.61 (m; 4H, Ph-CH$_2$—C$\underline{H}_2$—), 1.30-1.32 (m; 12H, —CH$_2$—), 0.88 ppm (t; 6H, —CH$_3$).

e) N,N'-Bis{3-[4-(N,N-di-n-hexylphenylamino)phenyl]propyl}-1,6,7,12-tetrachloroperylenetetracarboximide

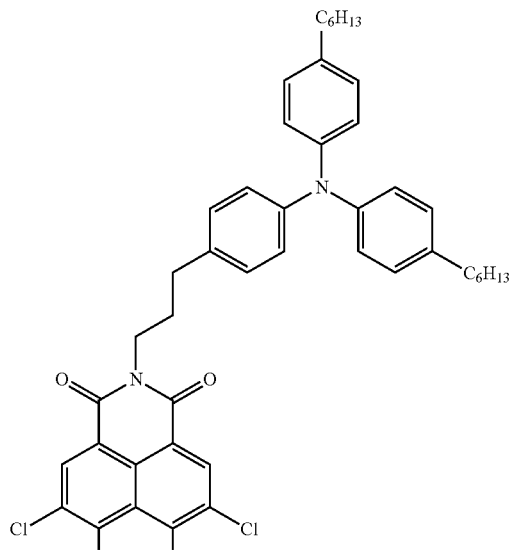

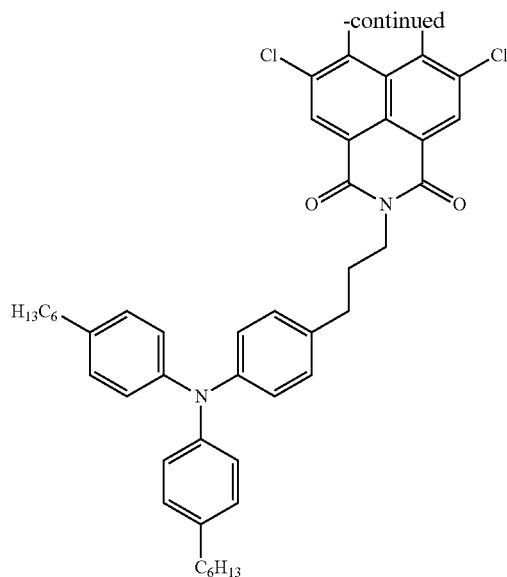

1.06 g (2.00 mmol) of 1,6,7,12-tetrachloroperylenetetracarboximide and 1.18 g (5.40 mmol) of 4-(3-aminopropyl)-N,N-di-(4-n-hexylphenyl)aniline were stirred at 80° C. in 20 ml of chlorobenzene under nitrogen for 12 hours. After the reaction mixture had been cooled to room temperature, it was concentrated to dryness under reduced pressure. The oil thus obtained was purified by chromatography on silica gel with methylene chloride/n-heptane (5:1). After the solvent had been removed, 1.28 g (45% of theory) of red-brown solid having an m.p. of 146° C. were obtained.

UV/Vis (methylene chloride): $\lambda_{max}$ ($\epsilon$)=518 nm (42070)

$C_{90}H_{92}Cl_4N_4O_4$ (M=1435.57 g/mol):

| calc. | C | 75.30 | H | 6.46 | Cl | 9.88 | N | 3.90 |
| found | C | 75.2 | H | 6.5 | Cl | 9.8 | N | 3.9 |

Example 11

Preparation of N,N'-bis{3-[4-(N,N-di-n-hexylphenylamino)phenyl]propyl}-1,7-dibromoperylenetetracarboximide

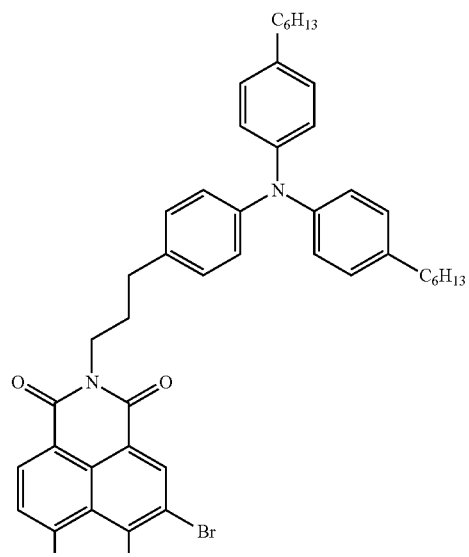

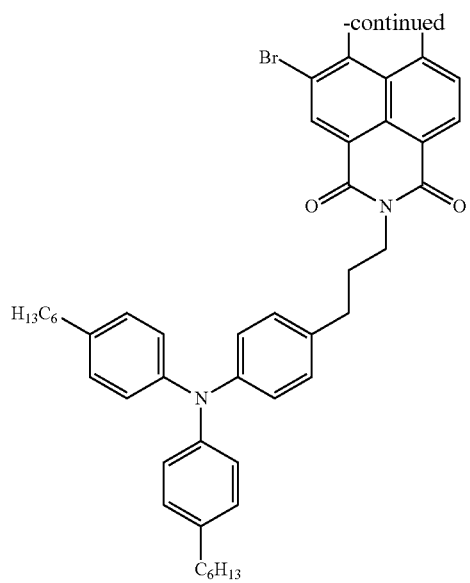

The preparation was effected correspondingly to that of example 10e with 3.00 g (5.45 mmol) of dibromoperylenetetracarboxylic dianhydride instead of 1,6,7,12-tetrachloroperylenetetracarboxylic dianhydride. 1.28 g (25% of theory) of red-brown solid were obtained.

UV/Vis (methylene chloride): $\lambda_{max}$ ($\epsilon$)=524 nm (50430)
$C_{90}H_{94}Br_2N_4O_4$ (M=1455.59 g/mol):

| | | | | | | | | | |
|---|---|---|---|---|---|---|---|---|---|
| calc. | C | 74.27 | H | 6.51 | Br | 10.98 | N | 3.85 | O | 4.40 |
| found | C | 74.8 | H | 6.9 | Br | 10.5 | N | 3.7 | O | 4.1 |

Example 12

Preparation of N,N'-bis{3-[4-(N,N-di-n-hexyloxyphenylamino)phenyl]-propyl}-1,7-dibromoperylenetetracarboximide a) N,N-(Di-4-n-hexyloxyphenyl)aniline

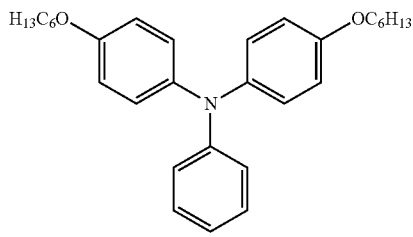

The preparation was effected correspondingly to that of example 10a) with 128 g (0.50 mol) of 4-bromo-n-hexyloxybenzene (prepared according to S. Sharma et al., Liquid Cryst. 2003, 30, 451-461). 81 g (81% of theory) of solid were obtained.

$^1$H NMR analysis:
$^1$H NMR (400 MHz, CDCl$_3$): δ=7.08 (mc, 2H, arom. H), 6.95 (mc; 4H, arom. H), 6.85 (mc; 2H, arom. H), 6.75 (mc; 5H, arom. H), 3.85 (t; 4H, O—CH$_2$—), 1.70 (mc; 4H, O—CH$_2$—CH$_2$—), 1.37 (mc; 4H, —CH$_2$—), 1.27 (mc; 8H, —CH$_2$—), 0.85 ppm (t; 6H, —CH$_3$).

b)
4-[N,N-(Di-4-n-hexyloxyphenyl)amino]benzaldehyde

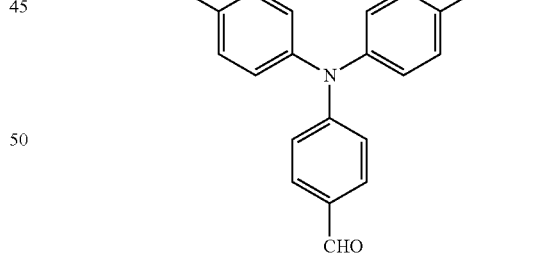

The preparation was effected correspondingly to that in example 10b). 130 g (0.29 mol) of N,N-(di-4-n-hexyloxyphenyl)aniline were used to obtain 111 g (81% of theory) of aldehyde.

$^1$H NMR analysis:
$^1$H NMR (400 MHz, CDCl$_3$): δ=9.75 (s; 1H, CHO), 7.62 (mc; 2H, arom. H), 7.11 (mc; 4H, arom. H), 6.86 (mc; 6H, arom. H), 3.95 (t; 4H, O—CH$_2$—), 1.79 (mc; 4H, c) 4-[N,N-(Di-4-n-hexyloxyphenyl)amino]cinnamonitrile

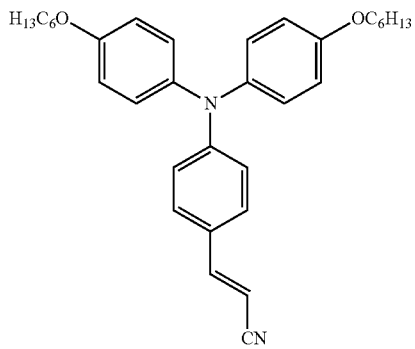

The preparation was effected correspondingly to that in example 10c). 69 g (0.145 mol) of 4-[N,N-(di-4-n-hexyloxyphenyl)amino]benzaldehyde were used to obtain 64 g (89% of theory) of nitrile.

$^1$H NMR analysis:

$^1$H NMR (400 MHz, CDCl$_3$): δ=7.19-7.27 (m; 3H, arom. H, =CH-Ph), 7.07 (mc; 4H, arom. H), 6.80-6.86 (m; 6H, arom. H), 5.61 (d; 1H, NC—CH=), 2.57 (t; 4H, Ph-CH$_2$—), 1.59-1.62 (m; 4H, O—CH$_2$—CH$_2$—), 1.32-1.36 (m; 12H, —CH$_2$—), 0.87 ppm (t; 6H, —CH$_3$).

d) 4-(3-Aminopropyl)-N,N-di-(4-n-hexyloxyphenyl)aniline

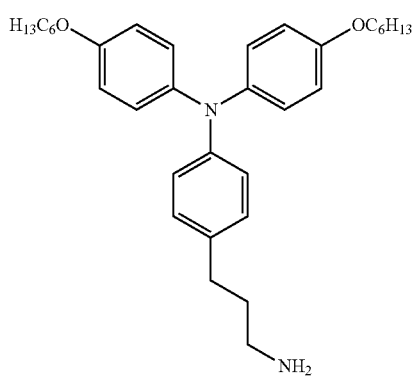

The preparation was effected correspondingly to that in example 10d). 47 g (0.195 mol) of 4-[N,N-di-4-n-hexyloxyphenyl)amino]cinnamonitrile were used to obtain 43.7 g (92% of theory) of oily amine.

$^1$H NMR analysis:

$^1$H NMR (400 MHz, CDCl$_3$): δ=6.97-7.01 (m; 6H, arom. H), 6.85-6.88 (m; 2H, arom. H), 6.76-6.80 (m; 4H, arom. H), 3.91 (t; 4H, O—CH$_2$—), 2.74 (t; 2H, —CH$_2$—NH$_2$), 2.57 (t; 2H, —CH$_2$-Ph), 1.72-1.79 (m; 6H, —CH$_2$—), 1.55 (mc; 2H, —CH$_2$—), 1.44 (mc; 4H, —CH$_2$—), 1.35 (mc; 8H, —CH$_2$—), 0.89 ppm (t; 6H, —CH$_3$).

e) N,N'-Bis{3-[4-(N,N-di-n-hexyloxyphenylamino)phenyl]propyl}-1,7-dibromoperylenetetracarboximide

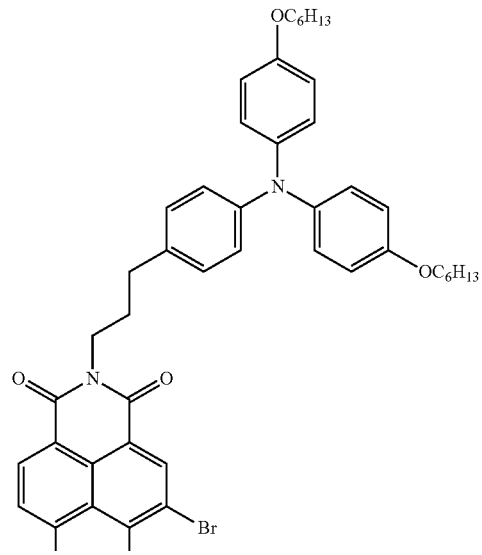

-continued

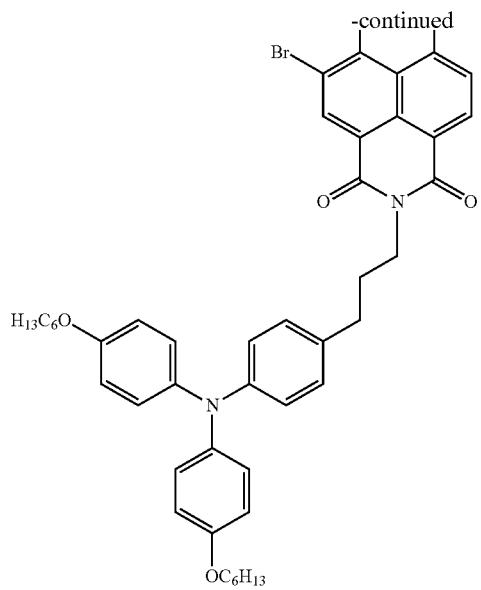

The preparation was effected correspondingly to that in example 10e) with 3.00 g (5.45 mmol) of dibromoperylenetetracarboxylic dianhydride. 3.68 g (44% of theory) of red microcrystals were obtained, which melted at 84-85° C.

UV/Vis (methylene chloride): $\lambda_{max}$ ($\epsilon$)=524 nm (52790)

$C_{90}H_{94}Br_2N_4O_8$ (M=1519.58 g/mol):

| calc. | C | 71.14 | H | 6.24 | Br | 10.52 | N | 3.69 | O | 8.42 |
|---|---|---|---|---|---|---|---|---|---|---|
| found | C | 71.0 | H | 6.4 | Br | 10.8 | N | 3.8 | O | 8.6 |

Example 13

Preparation of N,N'-bis[3-(3,6-di-n-hexyl-N-carbazolyl)propyl]-1,7-dicyanoperylenetetracarboximide

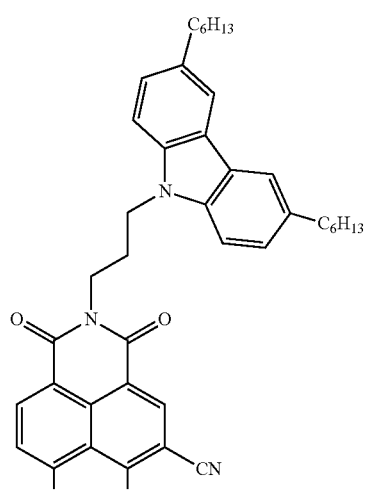

-continued

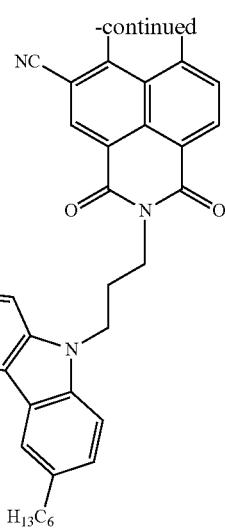

a) 2.50 g (1.92 mmol) of N,N'-bis[3-(3,6-di-n-hexyl-N-carbazolyl)propyl]-1,7-dibromoperylenetetracarboximide, 0.28 g (0.76 mmol) of potassium hexacyanoferrate(II), 0.070 g (0.385 mmol) of 98% copper iodide and 0.48 g (3.85 mmol) of 1-butylimidazole were added to 25 ml of 1,3,5-trimethylbenzene. The suspension was heated to boiling under reflux for 6 hours. After the reaction mixture had been cooled to room temperature, 80 ml of methanol were added. The precipitate was filtered off with suction, washed with methanol and dried (2.6 g). The crude product was dissolved in 80 ml of methylene chloride and purified by chromatography, on silica gel (60 Å, 60-200 µm). 1.72 g (19% of theory) of black solid were obtained.

b) A solution of 1.50 g (1.15 mmol) of N,N'-bis[3-(3,6-di-n-hexyl-N-carbazolyl)propyl]-1,7-dibromoperylenetetracarboximide in 15 ml of N-methylpyrrolidinone was admixed with 0.31 g (3.5 mmol) of copper cyanide and heated to 150° C. After stirring at this temperature for one hour, the reaction mixture was allowed to cool to room temperature. After 50 ml of methanol had been added, the reaction mixture was stirred briefly and then filtered. The residue was slurried with 8 ml of saturated sodium hydrogencarbonate solution, filtered off with suction, washed with water and then with methanol, and dried (1.3 g). The crude product was dissolved in 80 ml of methylene chloride and purified by chromatography on alumina (neutral, 58 Å) with methylene chloride/n-heptane (5:1). 0.65 g (47% of theory) of black solid were obtained, which melted at 242-244° C. According to $^1$H NMR, the substance comprised the 1,6-dicyano isomer as a by-product.

UV/Vis (methylene chloride): $\lambda_{max}$ (E)=524 nm (53700)
$C_{80}H_{82}N_6O_4$ (M=1191.58 g/mol):

| | | | | | | | |
|---|---|---|---|---|---|---|---|
| calc. | C | 80.64 | H | 6.94 | N | 7.05 | |
| found | C | 80.8 | H | 6.8 | N | 6.9 | |

Example 14

Preparation of N,N'-bis[4-(N,N-di-t-octylphenylamino)phenyl]-1,7-dicyano-perylenetetracarboximide

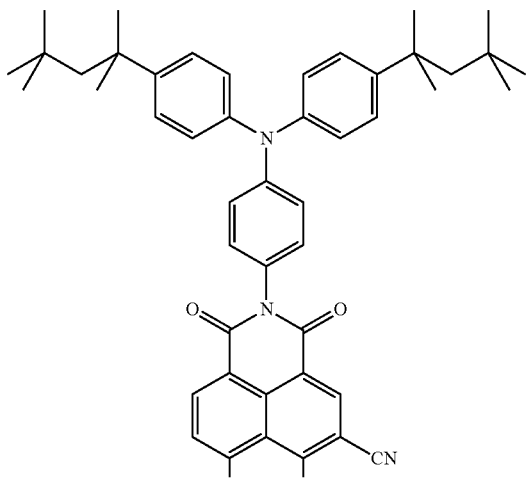

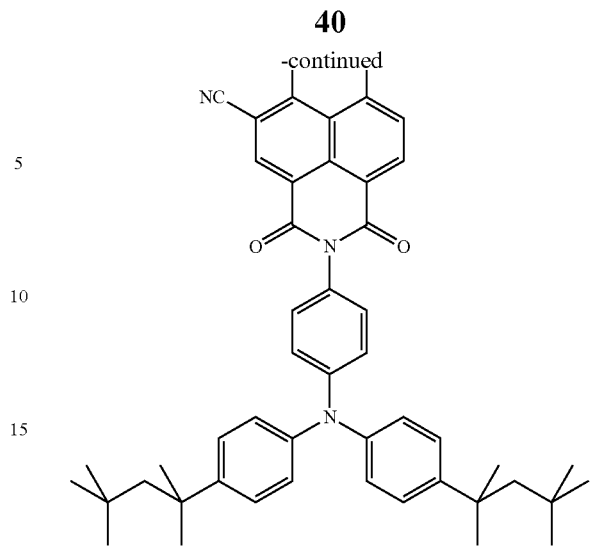

The preparation was effected correspondingly to that in example 13b) from 1.50 g (1.01 mmol) of N,N'-bis{4-[N,N-bis(1,1,3,3-tetramethylbutyl-4-phenyl)amino]phenyl}-1,7-dibromoperylenetetracarboximide. After recrystallization in nitroethane, 0.38 g (27% of theory) of dark red microcrystals were obtained, which melted at 333-334° C.

UV/Vis (methylene chloride): $\lambda_{max}$ (ε)=524 nm (71050)
$C_{94}H_{98}N_6O_4$ (M=1375.87 g/mol):

| | | | | | | | |
|---|---|---|---|---|---|---|---|
| calc. | C | 82.06 | H | 7.18 | N | 6.11 | O | 4.65 |
| found | C | 81.4 | H | 7.2 | N | 5.9 | O | 4.7 |

Example 15

Preparation of N,N'-bis{3-[4-(N,N-di-n-hexyloxyphenylamino)phenyl]-propyl}-1,7-dicyanoperylenetetracarboximide

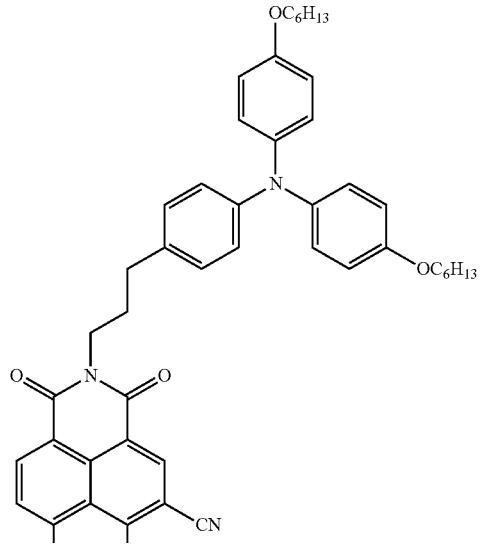

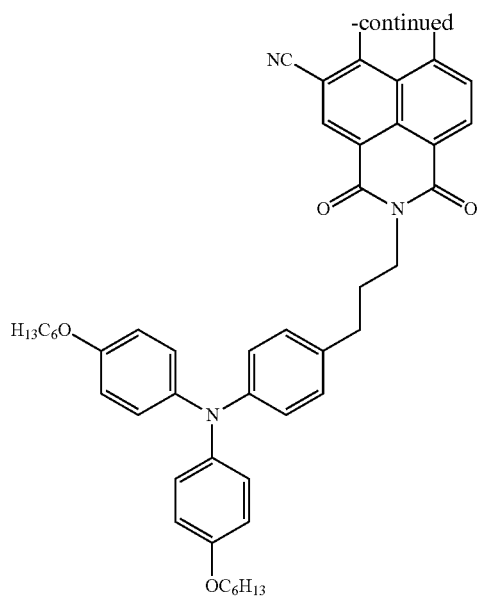

The preparation was effected correspondingly to that in example 13b) from 2.00 g (1.32 mmol) of N,N'-bis{3-[4-(N,N-di-n-hexyloxyphenylamino)phenyl]propyl}-1,7-dibromoperylenetetracarboximide. 1.06 g (57% of theory) of dark red microcrystals were obtained, which melted at 207° C.

UV/Vis (methylene chloride): $\lambda_{max}$ ($\epsilon$)=524 nm (60680)

$C_{92}H_{94}N_6O_8$ (M=1411.81 g/mol):

| calc. | C | 78.27 | H | 6.71 | N | 5.95 | O | 9.07 |
|---|---|---|---|---|---|---|---|---|
| found | C | 78.3 | H | 7.0 | N | 5.8 | O | 9.0 |

Example 16

Preparation of N,N'-bis[2-(3,6-di-n-hexyl-N-carbazolyl)ethyl]naphthalene-tetracarboximide

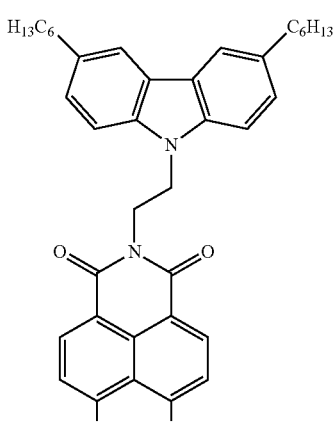

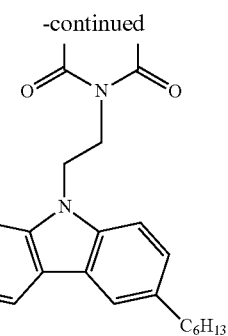

A solution of 1.50 g (5.31 mmol) of 95% 1,4,5,8-naphthalenetetracarboxylic dianhydride and 4.22 g (11.2 mmol) of N-(2-aminoethyl)-3,6-di-n-hexylcarbazole (see example 1d)) in 50 ml of NMP was heated at 120° C. for 2.5 hours. After cooling to room temperature, the reaction solution was admixed with 100 ml of methanol. The precipitate was filtered off with suction, washed and dried (5.29 g). The crude product was recrystallized in toluene. 4.41 g (84% of theory) of brown solid were obtained, which melted at 252° C.

UV/Vis (methylene chloride): $\lambda_{max}$ ($\epsilon$)=378 nm (30360)

$C_{56}H_{76}N_4O_4$ (M=989.37 g/mol):

| calc. | C | 80.13 | H | 7.74 | N | 5.66 | O | 6.47 |
|---|---|---|---|---|---|---|---|---|
| found | C | 80.2 | H | 7.6 | N | 5.7 | O | 6.4 |

Example 17

Preparation of N,N'-bis[3-(3,6-di-n-hexyl-N-carbazolyl)propyl]-naphthalenetetracarboximide

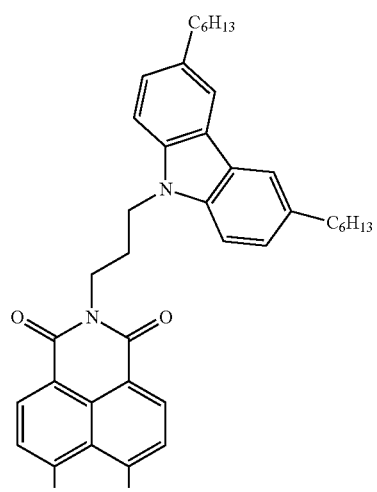

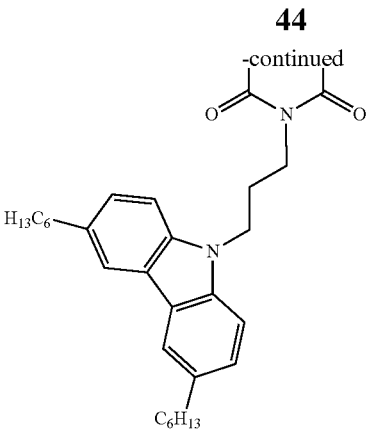

The preparation was effected correspondingly to that in example 17 with N-(3-aminopropyl)-3,6-di-n-hexylcarbazole. 1.50 g (5.31 mmol) of 1,4,5,8-naphthalene-tetracarboxylic dianhydride were used to obtain 4.53 g (80% of theory) of pale violet solid, which melted at 176-178° C.

UV/Vis (methylene chloride): $\lambda_{max}$ ($\epsilon$)=380 nm (26510)
$C_{68}H_{80}N_4O_4$ (M=1017.42 g/mol):

| calc. | C | 80.28 | H | 7.93 | N | 5.51 | O | 6.29 |
| found | C | 80.4 | H | 7.9 | N | 5.5 | O | 6.4 |

Example 18

Preparation of N,N'-Bis{3-[4-(N,N-di-n-hexylphenylamino)phenyl]propyl}-naphthalenetetracarboximide

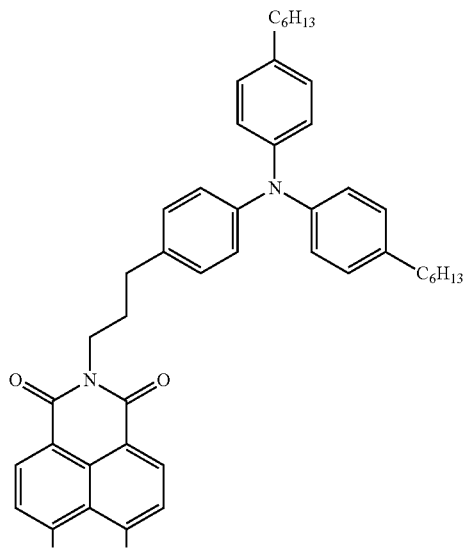

-continued

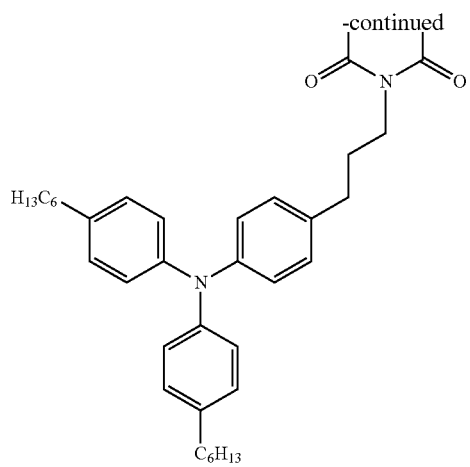

A solution of 1.58 g (5.59 mmol) of 95% 1,4,5,8-naphthalenetetracarboxylic dianhydride and 5.53 g (11.8 mmol) of 4-(3-aminopropyl)-N,N-di(4-n-hexylphenyl)aniline (see example 10d)) in 50 ml of toluene was heated at 80° C. for 5 hours. After cooling to room temperature, the reaction mixture was concentrated to dryness (dark blue oil). The crude product was purified by chromatography on silica gel (60 Å, 60-200 μm) with methylene chloride/n-heptane (4:1) as the eluent. 5.15 g (75% of theory) of blue resinous solid were obtained, which melted at 50-54° C.

UV/Vis (methylene chloride): $\lambda_{max}$ ($\epsilon$)=380 nm (28280)

$C_{80}H_{92}N_4O_4$ (M=1173.65 g/mol):

| | | | | | | | | |
|---|---|---|---|---|---|---|---|---|
| calc. | C | 81.87 | H | 7.90 | N | 4.77 | O | 5.45 |
| found | C | 81.8 | H | 8.0 | N | 4.7 | O | 5.5 |

Bluish colorless needles crystallized out of n-hexane, which melted at 104-105° C. The $^1$H NMR spectrum of this substance was identical to that of the blue resinous solid.

Example 19

Preparation of N,N'-bis{3-[4-(N,N-di-n-hexylphenylamino)phenyl]propyl}-pyromellitimide

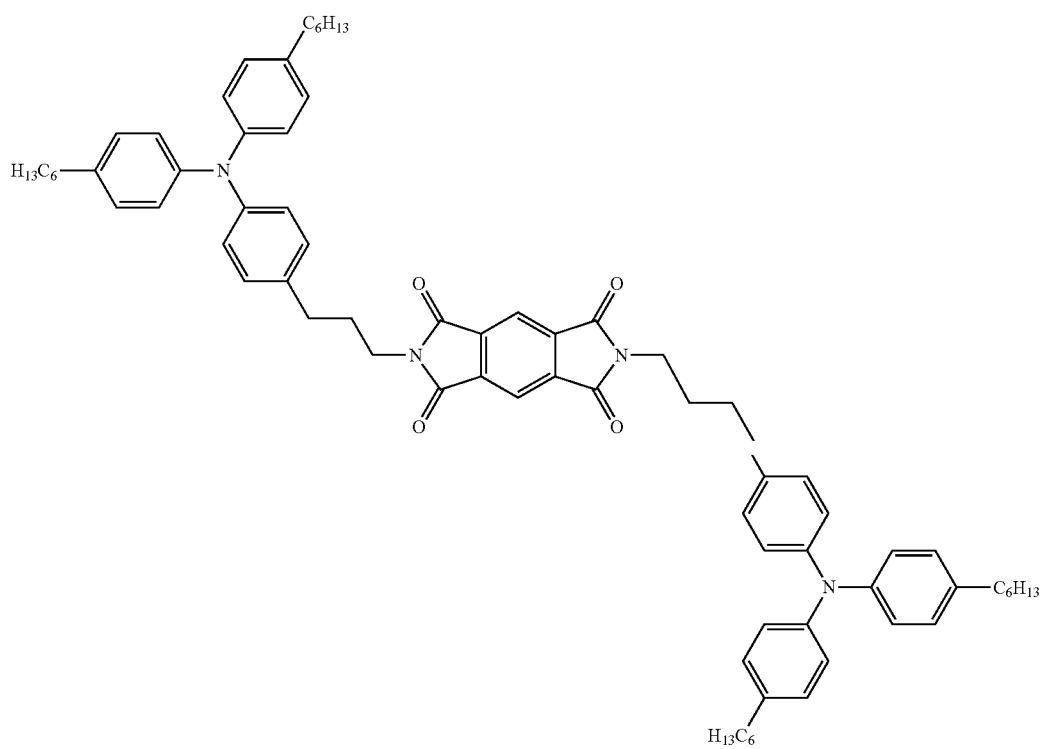

A solution of 3.00 g (13.8 mmol) of pyromellitic anhydride and 13.59 g (28.88 mmol) of 4-(3-aminopropyl)-N,N-di-(4-n-hexylphenyl)aniline (see example 10d)) in 50 ml of toluene was stirred at 100° C. under nitrogen for 6 hours. After cooling to room temperature, the reaction mixture was concentrated under reduced pressure down to a brown oil. The oil was purified by chromatography on silica gel (60 Å, 60-200 µm) with methylene chloride/methanol (20:1) as the eluent. A further purification was effected by recrystallization from nitroethane. 8.98 g (58% of theory) of pale violet solid were obtained, which melted at 112° C.

UV/Vis (methylene chloride): $\lambda_{max}$ ($\epsilon$)=304 nm (55925)
$C_{76}H_{90}N_4O_4$ (M=1133.59 g/mol):

| calc. | C | 81.24 | H | 8.07 | N | 4.99 | O | 5.70 |
|-------|---|-------|---|------|---|------|---|------|
| found | C | 81.2  | H | 8.2  | N | 5.0  | O | 5.8  |

Example 20

Preparation of N,N'-bis{3-[4-(N,N-di-n-hexyloxyphenylamino)phenyl]-propyl}pyromellitimide The preparation was effected correspondingly to that in example 19 with 3.00 g (13.8 mmol) of pyromellitic anhydride and 14.52 g (28.9 mmol) of 4-(3-aminopropyl)-N,N-di-(4-n-hexyloxyphenyl)aniline. 9.86 g (60% of theory) of pink needles were obtained, which melted at 135° C.

UV/Vis (methylene chloride): $\lambda_{max}$ ($\epsilon$)=302 nm (51670)
$C_{76}H_{90}N_4O_8$ (M=1187.59 g/mol):

| calc. | C | 76.87 | H | 7.64 | N | 4.72 | O | 10.78 |
|-------|---|-------|---|------|---|------|---|-------|
| found | C | 76.9  | H | 7.6  | N | 4.7  | O | 10.7  |

Example 21

Preparation of
3-(3,6-dimethyl-N-carbazolyl)propylammonium chloride a)
N-[3-(N-Phthalimido)propyl]-3,6-dimethylcarbazole

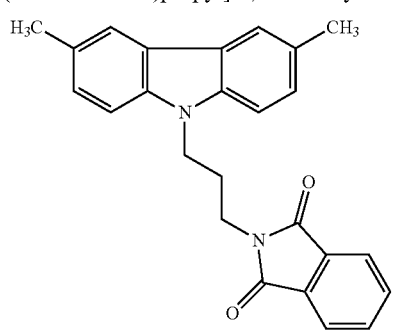

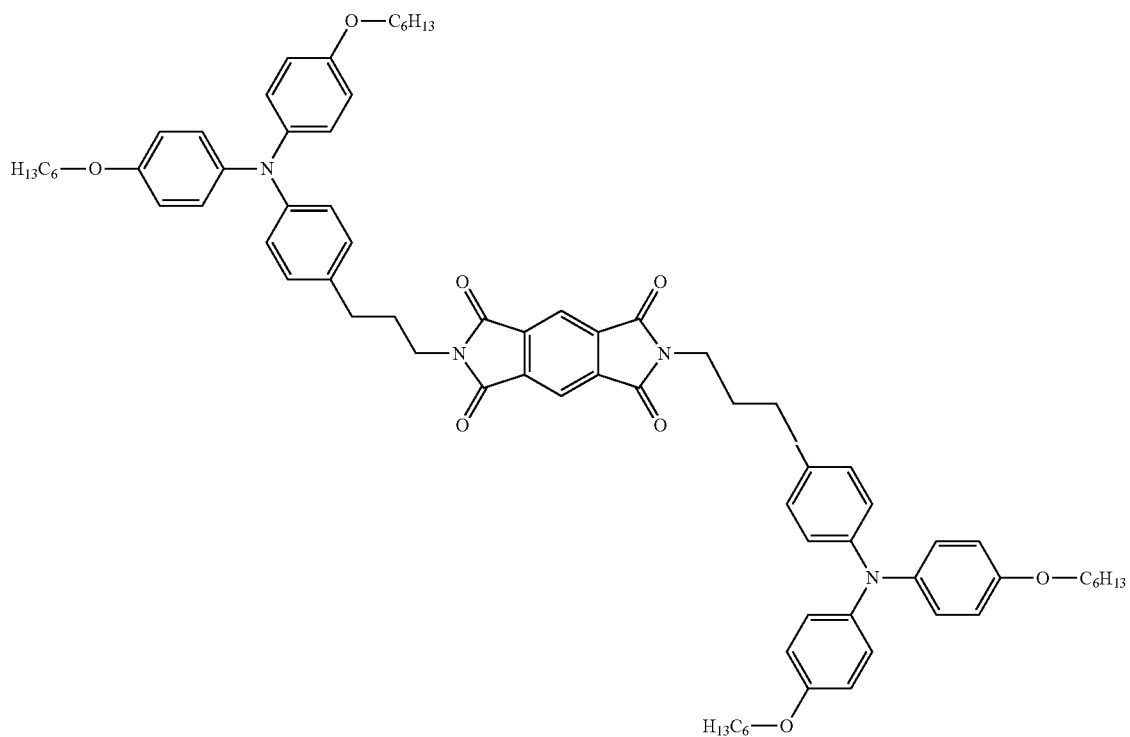

The preparation was effected correspondingly to that in example 2a). 9.76 g (50.0 mmol) of 3,6-dimethylcarbazole were used to prepare 18.32 g (96% of theory) of yellow microcrystals, which melted at 134-135° C.

b) 3-(3,6-Dimethyl-N-carbazolyl)propylammonium chloride

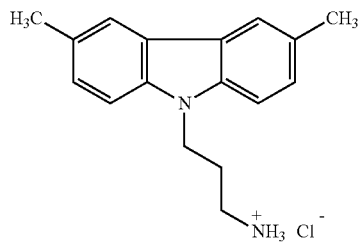

To a solution of 15.00 g (39.2 mmol) of N-[3-(N-phthalimido) propyl]-3,6-dimethyl-carbazole in 250 ml each of THF and ethanol were added 3.93 g (78.4 mmol) of 98% hydrazine monohydrate. The solution was heated to boiling under reflux for 20 hours, which precipitated a solid. After cooling to room temperature, 600 ml of water were added. After the organic solvents had been removed, 400 ml of diethyl ether were added and the mixture was adjusted to pH 13.5 with 62 ml of 20% NaOH. The aqueous phase was removed and extracted twice more with 150 ml each time of diethyl ether. The combined organic phases were dried over sodium sulfate, filtered and concentrated down to an oil, which was dissolved in 100 ml of methylene chloride and then admixed with 15 ml of conc. HCl, which precipitated a solid. This was filtered off with suction, washed with methylene chloride and n-pentane, and dried. 7.08 (63% of theory) of colorless crystals were obtained, which melted at 247° C.

$^1$H NMR analysis:

$^1$H NMR (D$_6$-DMSO, 400 MHz): δ=8.12 (s; 3H), 7.90 (s; 2H), 7.55 (d; 2H), 7.27 (d; 2H), 4.48 (t; 2H), 2.79 (t; 2H), 2.07 ppm (q; 2H)

Example 22

Preparation of N-[2-(4-diphenylaminophenyl)ethyl]pivalamide a) 4-(N,N-Diphenylamino)phenylacetonitrile

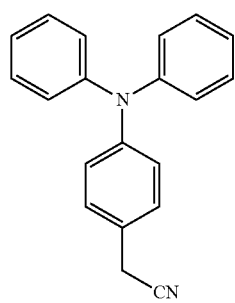 [SMILES: N#CCc1ccc(N(c2ccccc2)c2ccccc2)cc1]

A solution of 68.3 g (0.35 mol) of (p-toluenesulfonyl) methyl isocyanide (TOSMIC) in 300 ml of dimethoxyethane was added dropwise to a stirred suspension of 78 g (0.70 mol) of potassium tert-butoxide in 300 ml of dimethoxyethane at −30° C. under nitrogen. After the solution had been cooled to −55° C., a solution of 92 g (0.34 mol) of 4-(N,N-diphenylamino)benzaldehyde in 100 ml of dimethoxyethane was added dropwise. After stirring at −55° C. for 1 hour, methanol was added. The reaction solution was heated to boiling under reflux for 30 min. After the solution had been concentrated to dryness, the residue was taken up with 600 ml of water and 30 ml of acetic acid. The aqueous solution was extracted with methylene chloride. The combined organic phases were washed with a saturated sodium carbonate solution, dried over magnesium sulfate and concentrated to dryness. 75 g (79% of theory) of the desired nitrile were obtained.

$^1$H NMR analysis:

$^1$H NMR (CDCl$_3$, 400 MHz): δ=7.26 (mc; 5H, arom. H), 7.11 (mc; 2H, arom. H), 7.01 (mc; 7H, arom. H), 3.68 ppm (s; 2H, Ph-CH$_2$—CN)

b) N-[2-(4-Diphenylaminophenyl)ethyl]pivalamide

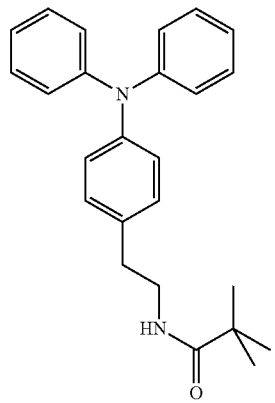 [SMILES: CC(C)(C)C(=O)NCCc1ccc(N(c2ccccc2)c2ccccc2)cc1]

To a solution, cooled to 0° C., of 150 g (0.528 mol) of 4-(N,N-diphenylamino)phenyl-acetonitrile in 500 ml of anhydrous methanol were added, with stirring, 153 g (0.70 mol) of di-tert-butyl pyrocarbonate and 1.25 g (53 mmol) of nickel chloride. 136.8 g (3.70 mol) of sodium borohydride were added in portions within 2 hours. After stirring for 30 min, the solvent was removed under reduced pressure. The reddish residue was dissolved in ethyl acetate and extracted by shaking with saturated sodium hydrogencarbonate solution. The organic phase was removed, dried over magnesium sulfate, filtered and concentrated to dryness. 100 g (49% of theory) of the protected amine were obtained.

$^1$H NMR analysis:

$^1$H NMR (CDCl$_3$, 400 MHz): δ=7.17 (mc; 4H, arom. H), 6.99 (mc; 6H, arom. H), 6.90 (mc; 4H, arom. H), 3.29 (m; 2H), 2.66 (m; 2H), 1.35 (s; 9H, —CH$_3$)

Example 23

Preparation of 4-(3-aminopropyl)-N,N-di(4-t-octylphenyl)aniline a) N,N-(Di-4-t-octylphenyl)aniline

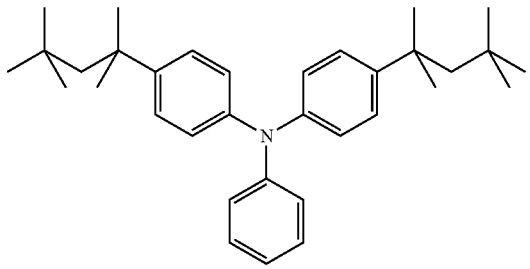 [SMILES: CC(C)(C)CC(C)(C)c1ccc(N(c2ccccc2)c2ccc(C(C)(C)CC(C)(C)C)cc2)cc1]

A mixture of 198.6 g (0.505 mol) of 4,4"-di-tert-octylphenylamine, 102.5 g (0.653 mol), 100 g (1.04 mol) of sodium tert-butoxide, 10 g (0.011 mol) of tris(dibenzylidene-acetone)dipalladium and 10 g (0.018 mol) of 1,1"-bis(diphenylphosphino)ferrocene in 1600 ml of toluene was heated at 90° C. with stirring for 16 hours. After cooling to room temperature, methylene chloride was added. The solution was filtered and concentrated to dryness under reduced pressure. The residue was taken up with methylene chloride and purified by chromatography on silica gel with petroleum ether as the eluent. 210 g (88% of theory) of the desired triarylamine were obtained.

$^1$H NMR analysis:

$^1$H NMR (CDCl$_3$, 400 MHz): δ=7.22 (mc; 6H, arom. H), 7.03 (mc; 2H, arom. H), 6.98 (mc; 4H, arom. H), 6.95 (mc; 1H, arom. H), 1.71 (s; 4H, —CH$_2$—), 1.36 (s; 12H, Ph-C(CH$_3$)$_2$—), 0.76 ppm (s; 18H, —C(CH$_3$)$_3$)

b) 4-[N,N-(Di-4-t-octylphenyl)amino]benzaldehyde

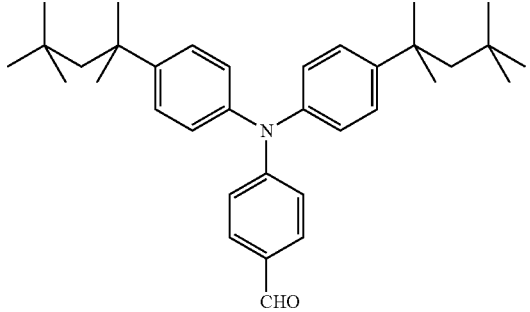 [SMILES: CC(C)(C)CC(C)(C)c1ccc(N(c2ccc(C=O)cc2)c2ccc(C(C)(C)CC(C)(C)C)cc2)cc1]

The preparation was effected correspondingly to that in example 10b). 290 g (0.618 mol) of N,N-(di-4-t-octylphenyl)aniline were used to obtain 250 g (83% of theory) of aldehyde.

$^1$H NMR analysis:

$^1$H NMR (CDCl$_3$, 400 MHz): δ=9.78 (s; 1H, —CHO), 7.65 (d; 2H, arom. H), 7.33 (d; 4H, arom. H), 7.06 (d; 4H, arom. H), 6.95 (d; 2H, arom. H), 1.73 (s; 4H, —CH$_2$—), 1.36 (s; 12H, Ph-C(CH$_3$)$_2$—), 0.75 ppm (s; 18H, —C(CH$_3$)$_3$)

c) 4-[N,N-(Di-4-t-octylphenyl)amino]cinnamonitrile

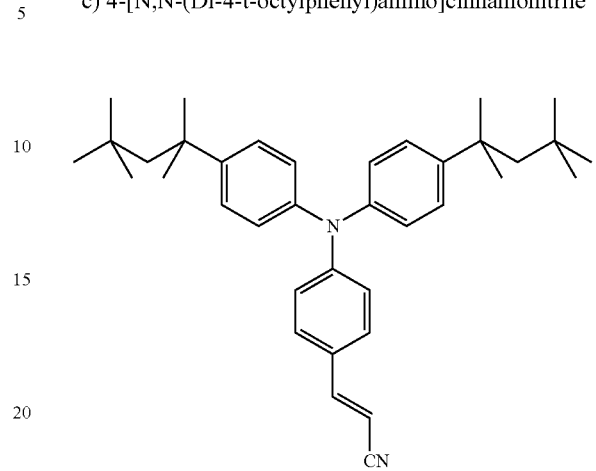

The preparation was effected correspondingly to that in example 10c). 52.7 g (0.298 mol) of 4-[N,N-(di-4-t-octylphenyl)amino]benzaldehyde were used to obtain 140 g (96% of theory) of nitrile.

$^1$H NMR analysis:

$^1$H NMR (CDCl$_3$, 400 MHz): δ=7.23-7.31 (m; 7H, arom. H, —CH=CH—CN), 7.03 (mc; 4H, arom. H), 6.93 (mc; 2H, arom. $\overline{H}$), 5.64 (d; 1H, —CH=$\overline{CH}$—CN), 1.73 (s; 4H, —CH$_2$—), 1.36 (s; 12H, Ph-C(CH$_3$)$\overline{_2}$—), 0.75 ppm (s; 18H, —C(CH$_3$)$_3$)

d) 4-(3-Aminopropyl)-N,N-di(4-t-octylphenyl)aniline

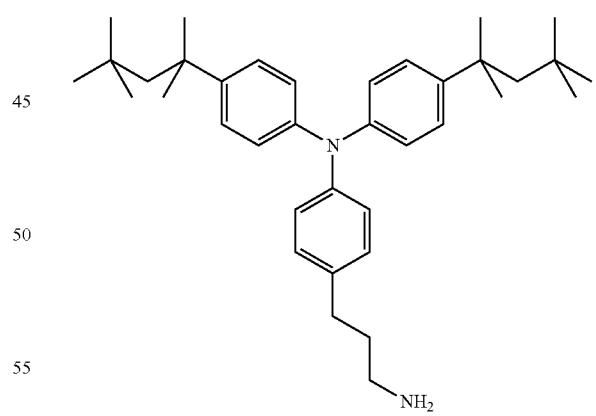

The preparation was effected correspondingly to that in example 10d). 130 g (0.250 mol) of 4-[N,N-(di-4-t-octylphenyl)amino]cinnamonitrile were used to obtain 93 g (70% of theory) of amine.

$^1$H NMR analysis:

$^1$H NMR (CDCl$_3$, 400 MHz): δ=7.20 (mc; 4H, arom. H), 7.03 (mc; 2H, arom. H), 6.95 (mc; 6H, arom. H), 2.77 (t; 2H, —C$\underline{H}_2$—NH$_2$), 2.60 (t; 2H, Ph-CH$_2$—), 2.02 (s, broad; 2H, —NH$_2$), 1.75-1.83 (m; 2H, —CH$_2$—CH$_2$—CH$_2$—), 1.69 (s; 4H, —CH$_2$—), 1.34 (s; 12H, Ph-C(CH$_3$)$_2$—), 0.75 ppm (s; 18H, —C(CH$_3$)$_3$)

Example 24

Preparation of
3-[N,N-(Di-4-hexylphenyl)-4-anilino]propanethiol a) Ethyl 4-[N,N-(di-4-hexylphenyl)amino]cinnamate

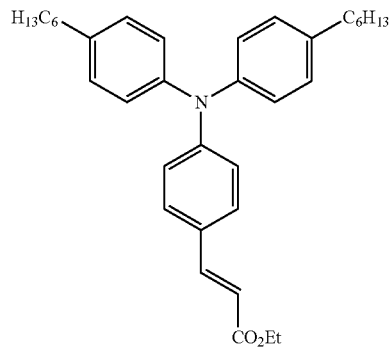

To a solution of 46.5 g (0.207 mol) of diethyl diethoxyphosphorylacetate in 2500 ml of anhydrous THF were added 85 ml (2.5 mol/l) of n-butyllithium at −78° C. under nitrogen. After stirring at −78° C. for two hours, a solution of 85.0 g (0.193 mol) of 4-[N,N-(di-4-n-hexylphenyl)amino]benzaldehyde in 800 ml of anhydrous THF was added. Subsequently, the reaction mixture was allowed to come to room temperature while stirring within 3 hours. 800 ml of water were added. The mixture was extracted with ethyl acetate. The combined organic phases were dried, filtered and concentrated to dryness. The crude product was purified by chromatography on silica gel. 80 g (81% of theory) of the desired cinnamic ester were obtained.

$^1$H NMR (400 MHz, CDCl$_3$): δ=7.53 (mc, 1H), 7.26 (mc, 1H), 7.26 (mc, 2H), 6.95-7.03 (m, 8H), 6.86 (m, 2H), 6.16-6.20 (m, 1H), 4.12-4.20 (m, 2H), 2.48-2.52 (t, 4H), 1.50-1.57 (m, 4H), 1.19-1.30 (m, 15H), 0.83 ppm (t, 6H).

b) Ethyl
3-[N,N-(di-4-hexylphenyl)-4-anilino]propionate

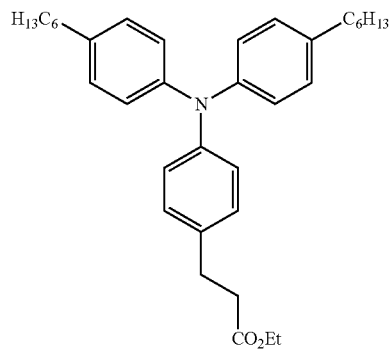

A solution of 82 g (0.16 mol) of ethyl 4-[N,N-(di-4-hexylphenyl)amino]cinnamate in 400 ml of tetrahydrofuran was stirred in a hydrogen atmosphere in the presence of 18 g of palladium catalyst (10% by weight on activated carbon) at room temperature. After 24 hours, the reaction mixture was filtered through a layer of Celite in order to remove the catalyst. Concentration of the filtrate to dryness gave 78 g (95% of theory) of the ester.

$^1$H NMR (400 MHz, CDCl$_3$): δ=6.88-7.00 (m, 12H), 4.04-4.09 (m, 2H), 2.79-2.83 (m, 2H), 2.45-2.55 (m, 6H), 1.49-1.56 (m, 4H), 1.15-1.29 (m, 15H), 0.83 ppm (mc, 6H).

c) 3-[N,N-(Di-4-hexylphenyl)-4-anilino]propanol

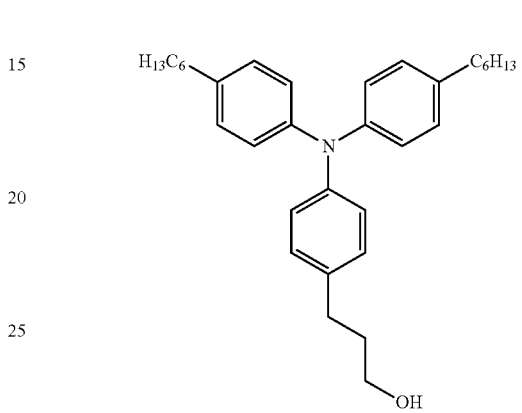

To a solution of 10.5 g (0.276 mol) of lithium aluminum hydride in 1000 ml of tetra-hydrofuran were added 70.8 g (0.138 mol) of ethyl 3-[N,N-(di-4-hexylphenyl)-4-anilino]propionate at room temperature under nitrogen. After the addition had ended, the solution was heated to 60° C. and stirred at this temperature for 24 hours. After cooling to room temperature, water was added until no further hydrogen was found. After filtration and drying with sodium sulphate, the solution was concentrated to dryness. 61 g (93% of theory) of the desired alcohol were obtained.

$^1$H NMR (400 MHz, CDCl$_3$): δ=6.88-7.01 (m, 12H), 3.60-3.69 (m, 4H), 5.58-5.60 (t, 2H), 2.57-2.61 (t, 2H), 2.51-2.55 (t, 4H), 1.76-1.85 (m, 4H), 1.42-1.56 (m, 4H), 1.15-1.29 (m, 15H), 0.82-0.84 ppm (t, 6H).

d) 4-(3-Bromopropyl)-N,N-(di-4-hexylphenyl)
aniline

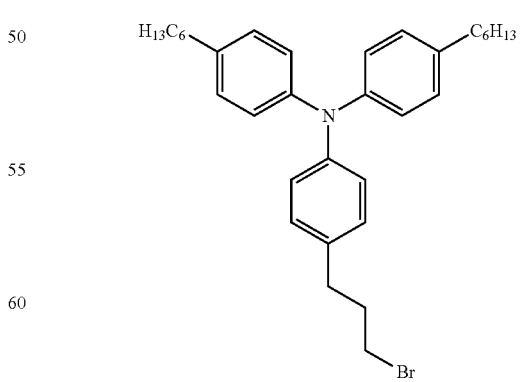

60 g (0.125 mol) of 3-[N,N-(di-4-hexylphenyl)-4-anilino] propanol were dissolved in 600 ml of 40% HBr. The solution was heated to 80° C. and stirred at this temperature for 24 hours. After cooling to room temperature, the solution was extracted with methylene chloride. The combined organic phases were dried over sodium sulfate, filtered and concentrated to dryness. 62 g (94% of theory) of the amine were obtained.

$^1$H NMR (400 MHz, CDCl$_3$): δ=6.88-7.01 (m, 12H), 3.32-3.36 (t, 2H), 2.62-2.66 (t, 2H), 2.45-2.49 (t, 4H), 2.04-2.11 (m, 2H), 1.48-1.56 (m, 4H), 1.23-1.31 (m, 12H), 0.82-0.84 ppm (m, 6H).

e) 3-[N,N-(Di-4-hexylphenyl)-4-anilino]propanethiol

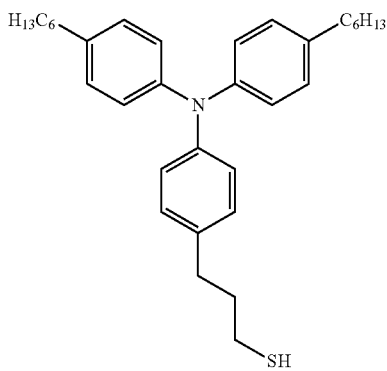

A mixture of 53.3 g (0.10 mol) of 4-(3-bromopropyl)-N,N-(di-4-hexylphenyl)aniline and 9.6 g (0.10 mol) of thiourea in 300 ml of ethanol was heated to boiling under reflux for 48 hours. After the addition of 50 ml of 40% NaOH, the reaction mixture was stirred at 60° C. for 4 hours. After cooling, it was extracted with methylene chloride. The combined organic phases were dried and then concentrated to dryness. 36.5 g (75% of theory) of the desired thiol were obtained.

$^1$H NMR (400 MHz, CDCl$_3$): δ=6.91-7.01 (m, 12H), 2.63-2.71 (m, 3H), 2.50-2.54 (m, 5H), 1.88-2.00 (m, 2H), 1.54-1.61 (m, 4H), 1.25-1.36 (m, 12H), 0.82-0.84 ppm (m, 6H).

Example 25

Preparation of 3-[N,N-(di-4-hexyloxyphenyl)-4-anilino]propanethiol a) Ethyl 4-[N,N-(di-4-hexyloxyphenyl)amino]cinnamate

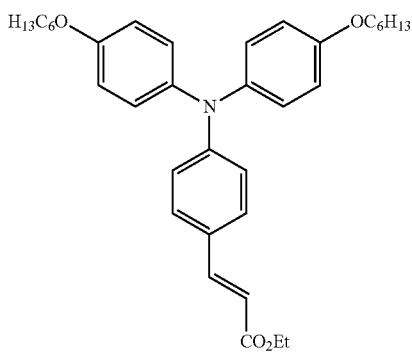

The preparation was effected correspondingly to that of ethyl 4-[N,N-(di-4-hexylphenyl)-amino]cinnamate (Example 24a). 140 g (0.296 mol) of 4-[N,N-(di-4-n-hexyloxyphenyl)-amino]benzaldehyde (Example 12b) were used to obtain 130 g (81% of theory) of the cinnamic ester.

$^1$H NMR (400 MHz, CDCl$_3$): δ=7.59 (mc, 1H), 7.30 (mc, 2H), 7.04-7.08 (m, 4H), 6.82-6.86 (m, 6H), 6.23 (mc, 1H), 4.21-4.26 (m, 2H), 3.93 (t, 4H), 1.74-1.81 (m, 4H), 1.30-1.50 (m, 15H), 0.93 ppm (t, 6H).

b) Ethyl 3-[N,N-(di-4-hexyloxyphenyl)-4-anilino]propionate

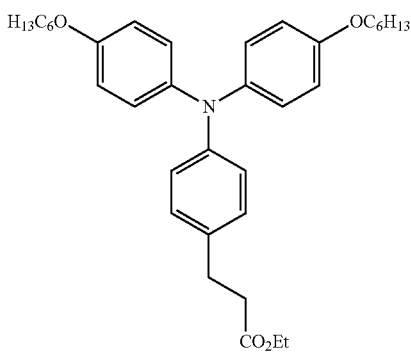

The preparation was effected correspondingly to that of ethyl 3-[N,N-(di-4-hexylphenyl)-4-anilino]propionate (Example 24b). 182 g (0.335 mol) of ethyl 4-[N,N-(di-4-hexyloxyphenyl)amino]cinnamate (Example 25a) were used to obtain 178 g (97% of theory) of the propionic ester.

$^1$H NMR (400 MHz, CDCl$_3$): δ=6.78-7.01 (m, 12H), 4.11-4.16 (m, 2H), 3.92 (t, 4H), 2.85-2.89 (m, 2H), 2.57-2.59 (m, 2H), 1.73-1.80 (m, 4H), 1.23-1.50 (m, 15H), 0.92 ppm (t, 6H).

c) 3-[N,N-(Di-4-hexyloxyphenyl)-4-anilino]propanol

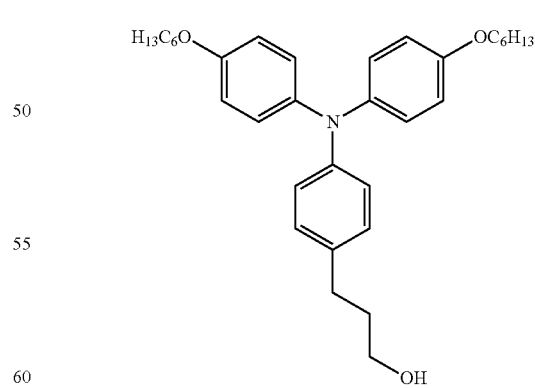

The preparation was effected correspondingly to that of 3-[N,N-(di-4-hexylphenyl)-4-anilino]propanol (Example 24c). 178 g (0.327 mol) of ethyl 3-[N,N-(di-4-hexyloxyphenyl)-4-anilino]propionate (Example 25b) were used to obtain 161 g (98% of theory) of the alcohol.

¹H NMR (400 MHz, CDCl₃): δ=7.01 (mc, 6H), 6.87 (mc, 2H), 6.70 (mc, 4H), 3.92 (t, 4H), 3.67 (mc, 2H), 2.62 (mc, 2H), 1.88 (mc, 2H), 1.78 (mc, 4H), 1.46 (mc, 4H), 1.34 (mc, 8H), 0.90 ppm (t, 6H).

d) 4-(3-Bromopropyl)-N,N-(di-4-hexyloxyphenyl) aniline

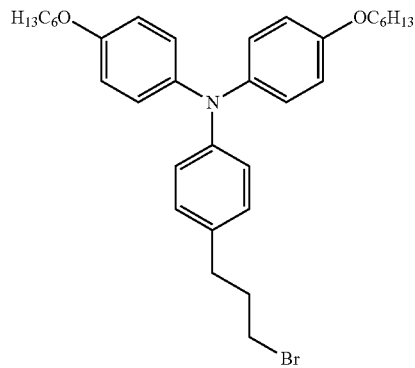

The preparation was effected correspondingly to that of 4-(3-bromopropyl)-N,N-(di-4-hexylphenyl)aniline (Example 24d). 60 g (0.125 mol) of 3-[N,N-(di-4-hexyloxyphenyl)-4-anilino]propanol (Example 25c) were used to obtain 62 g (94% of theory) of the amine.

¹H NMR (400 MHz, CDCl₃): δ=7.01 (mc, 6H), 6.89 (mc, 2H), 6.70 (mc, 4H), 3.93 (t, 4H), 3.42 (t, 2H), 2.70 (t, 2H), 2.16 (mc, 2H), 1.77 (mc, 4H), 1.47 (mc, 4H), 1.35 (mc, 8H), 0.92 ppm (t, 6H).

e) 3-[N,N-(Di-4-hexyloxyphenyl)-4-anilino]propanethiol

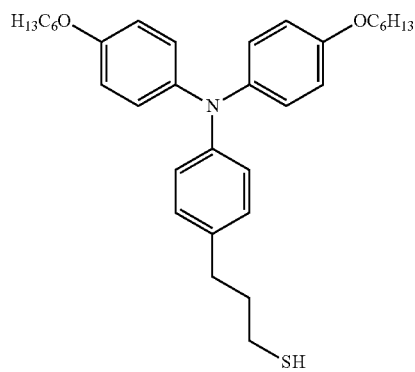

The preparation was effected correspondingly to that of 3-[N,N-(di-4-hexylphenyl)-4-anilino]propanethiol (Example 24e). 164 g (0.29 mol) of 4-(3-bromopropyl)-N,N-(di-4-hexyloxyphenyl)aniline (Example 25d) were used to obtain 102 g (68% of theory) of the thiol.

¹H NMR (400 MHz, CDCl₃): δ=7.02 (mc, 6H), 6.88 (mc, 2H), 6.81 (mc, 4H), 3.92 (t, 4H), 2.67 (mc, 2H), 2.56 (mc, 2H), 1.90 (mc, 2H), 1.78 (mc, 4H), 1.47 (mc, 4H), 1.35 (mc, 8H), 0.92 ppm (t, 6H).

Example 26

Preparation of 4-(3-aminopropyl)-N,N-di-(4-tolyl)aniline a) Ethyl 4-[N,N-(di-4-tolyl)amino]cinnamate

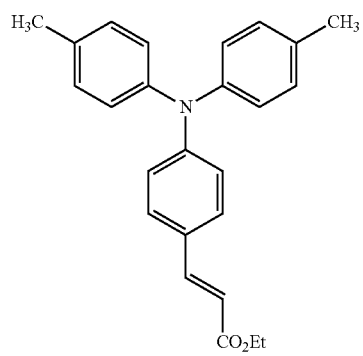

The preparation was effected correspondingly to that of 4-[N,N-(di-4-n-hexylphenyl)-amino]cinnamonitrile (Example 10c). 104.3 g (0.347 mol) of 4-[N,N-(di-4-tolyl)-amino]benzaldehyde were used to obtain 80 g (71%) of the cinnamic ester.

¹H NMR (400 MHz, CDCl₃): δ=7.24 (d, 1H), 7.21 (mc, 2H), 7.09 (mc, 4H), 7.01 (mc, 4H), 6.90 (mc, 2H), 5.61 (d, 1H), 2.32 ppm (s, 6H).

b) 4-(3-Aminopropyl)-N,N-di-(4-tolyl)aniline

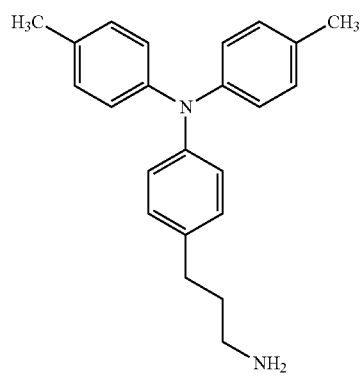

The preparation was effected correspondingly to that of 4-(3-aminopropyl)-N,N-di-(4-n-hexylphenyl)aniline (Example 10d). 100 g (0.309 mol) of ethyl 4-[N,N-(di-4-tolyl)amino]-cinnamate (Example 26a) were used to obtain 78.7 g (81%) of the amine.

¹H NMR (400 MHz, CDCl₃): δ=7.01 (mc, 6H), 6.96 (mc, 6H), 2.92 (s, 2H), 2.75 (t, 2H), 2.58 (mc, 2H), 2.27 (s, 6H), 1.79 ppm (m, 2H).

Example 27

Preparation of 4-(3-aminopropyl)-N,N-di-(4-methoxyphenyl)aniline a) 4-[N,N-(Di-4-methoxyphenyl)amino]cinnamonitrile

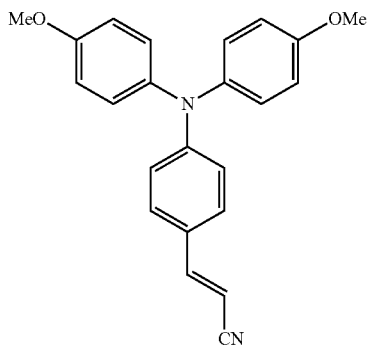 [SMILES: COc1ccc(N(c2ccc(/C=C/C#N)cc2)c2ccc(OC)cc2)cc1]

The preparation was effected correspondingly to that of 4-[N,N-(di-4-n-hexylphenyl)-amino]cinnamonitrile (Example 10c). 170.6 g (0.386 mol) of 4-[N,N-(di-4-methoxyphenyl)amino]benzaldehyde were used to obtain 150 g (84%) of the cinnamonitrile.

¹H NMR (400 MHz, CDCl₃): δ=7.20-7.25 (m; 3H, arom. H, =CH-Ph), 7.07-7.10 (m; 4H, arom. H), 6.87 (m; 4H, arom. H), 6.80-6.85 (m; 2H, arom. H), 5.60 (d; 1H, NC—CH=), 3.81 ppm (s, 6H, —OCH₃).

b) 4-(3-Aminopropyl)-N,N-di-(4-methoxyphenyl)aniline

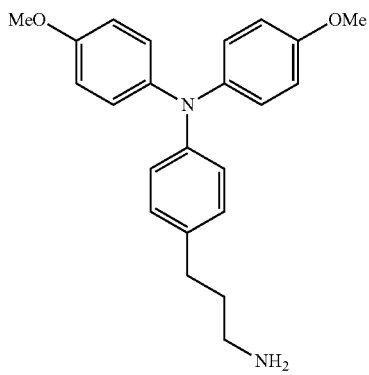 [SMILES: COc1ccc(N(c2ccc(CCCN)cc2)c2ccc(OC)cc2)cc1]

The preparation was effected correspondingly to that of 4-(3-aminopropyl)-N,N-di-(4-n-hexylphenyl)aniline (Example 10d). 70 g (0.196 mol) of 4-[N,N-(di-4-methoxyphenyl)-amino]cinnamonitrile (Example 27a) were used to obtain 43.7 g (60%) of the amine.

¹H NMR (400 MHz, CDCl₃): δ=6.95-7.00 (m, 6H), 6.86 (mc, 2H), 6.75-6.84 (m, 6H), 3.76 (s, 6H), 2.81 (t, 2H), 2.6-2.8 (broad, 2H), 2.58 (mc, 2H), 1.84 ppm (mc, 2H).

Example 28

Preparation of N,N-(di-4-hexyloxyphenyl)-p-phenylenediamine a) Di-(4-hexyloxyphenyl)amine

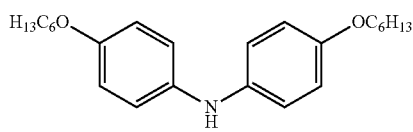

A solution of 118 g (0.61 mol) of 4-hexyloxyaniline, 130 g (0.51 mol) of 4-bromohexyl-oxybenzene, 146.9 (1.52 mol) of sodium tert-butoxide, 13.96 g (0.015 mol) of dipalladium tris(dibenzylideneacetone) and 8.46 g (0.015 mol) of 1,1"-bis (diphenyl-phosphino)ferrocene in 780 ml of toluene was heated at 90° C. for 16 hours. After cooling to room temperature, the solution was admixed with methylene chloride and then filtered. The filtrate was concentrated under reduced pressure, taken up in methylene chloride and chromatographed over silica gel with petroleum ether as the eluent. 120 g (64% of theory) of amine were obtained.

¹H NMR (400 MHz, D₆-DMSO): δ=7.44 (s, 1H), 6.86 (mc, 4H), 6.76 (mc, 4H), 3.83 (t, 4H), 1.63 (mc, 4H), 1.37 (mc, 4H), 1.26 (mc, 8H), 0.85 ppm (t, 6H).

b) N,N-(Di-4-hexyloxyphenyl)-4-nitroaniline

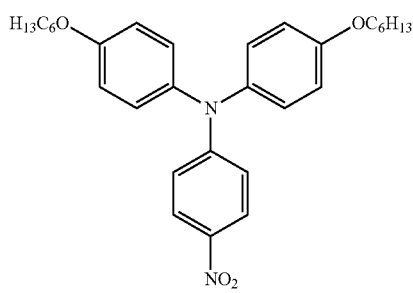

To a solution of 177.7 g (0.48 mol) of di(4-hexyloxyphenyl)amine and 161.3 g (1.44 mol) of potassium tert-butoxide in 1300 ml of dimethylformamide were added dropwise, at 0° C., 169.5 g (1.20 mol) of 1-fluoro-4-nitrobenzene. The reaction mixture was warmed to room temperature and stirred overnight. Once the solvent had been removed under reduced pressure, the residue was taken up with methylene chloride and chromatographed on silica gel with petroleum ether as the eluent. 150 g (64% of theory) of amine were obtained.

$^1$H NMR (400 MHz, CDCl$_3$): δ=7.91 (mc, 2H), 7.04 (mc, 4H), 6.82 (mc, 4H), 6.70 (mc, 2H), 3.88 (t, 4H), 1.71 (mc, 4H), 1.39 (mc, 4H), 1.29 (mc, 8H), 0.84 ppm (t, 6H).

c) N,N-(Di-4-hexyloxyphenyl)-p-phenylenediamine

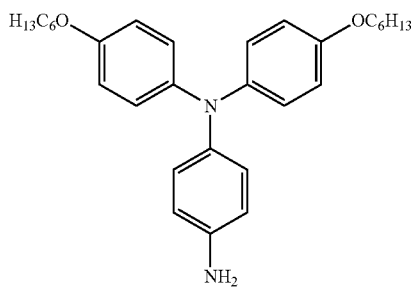

To a solution of 150 g (0.306 mol) of N,N-(di-4-hexyloxyphenyl)-4-nitroaniline in 750 ml of tetrahydrofuran was added palladium/carbon (10% by weight). The reaction mixture was stirred in a hydrogen atmosphere overnight. Subsequently, the solvent was removed under reduced pressure. 130 g (92% of theory) of amine were obtained.

$^1$H NMR (400 MHz, D$_6$-DMSO): δ=6.75 (mc, 8H), 6.69 (mc, 2H), 6.50 (mc, 2H), 4.89 (s, 2H), 3.85 (t, 4H), 1.63-1.66 (m, 4H), 1.34-1.39 (m, 4H), 1.17-1.29 (m, 8H), 0.85 ppm (t, 6H).

Example 29

Preparation of N,N'-bis[4-(N,N-di-t-octylphenylamino)phenyl]perylenebis-(dicarboximide)

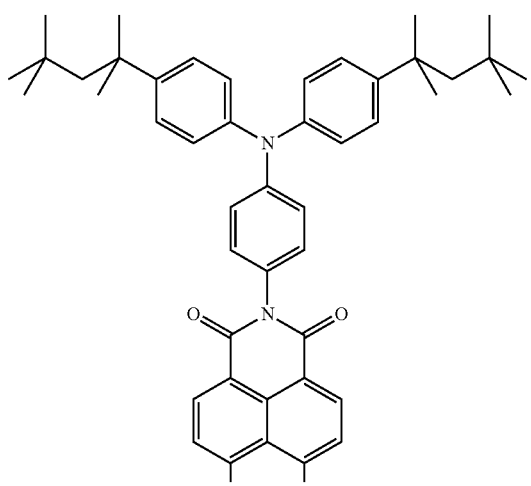

-continued

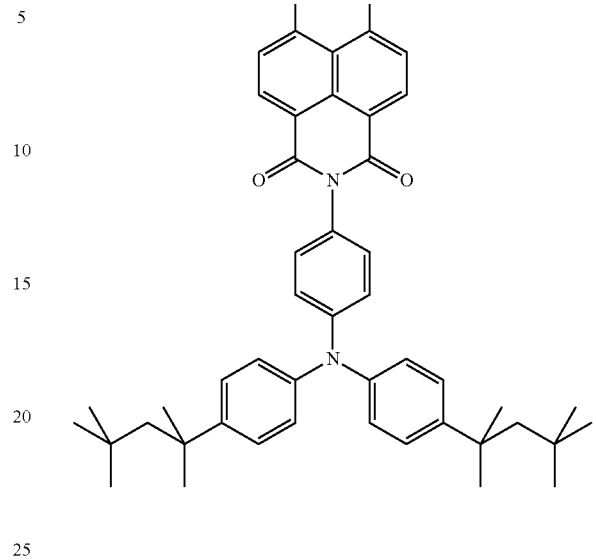

1.18 g (3.00 mmol) of perylenetetracarboxylic dianhydride, 3.64 g (7.50 mmol) of N,N-bis[4-(1,1,3,3-tetramethylbutyl)phenyl]-p-phenylenediamine and 0.075 g (0.038 mmol) of zinc acetate were added to 30 ml of N-methylpyrrolidinone and heated at 140° C. for 48 hours. After cooling to room temperature, 60 ml of methanol were added. The precipitate was filtered off with suction, washed with methanol and water, and dried (3.87 g). The crude product was purified by chromatography on silica gel (60 Å, 60-200 μm) with toluene/ethyl acetate (15:2). Subsequently, the substance was recrystallized in 150 ml of tert-amyl alcohol. 1.00 g (33% of theory) of solid with a m.p. of 364° C. were obtained.

UV/vis (methylene chloride): $\lambda_{max}$ (ε)=526 nm (98190)
C$_{92}$H$_{100}$N$_4$O$_4$ (M=1325.65 g/mol):

| calc. | C | 83.34 | H | 7.60 | N | 4.23 | O | 4.83 |
|---|---|---|---|---|---|---|---|---|
| found | C | 82.8 | H | 7.8 | N | 4.2 | O | 5.2 |

Example 30

Preparation of N,N'-bis{3-[4-(N,N-di-n-hexyloxyphenylamino)phenyl]-propyl}perylenebis(dicarboximide)

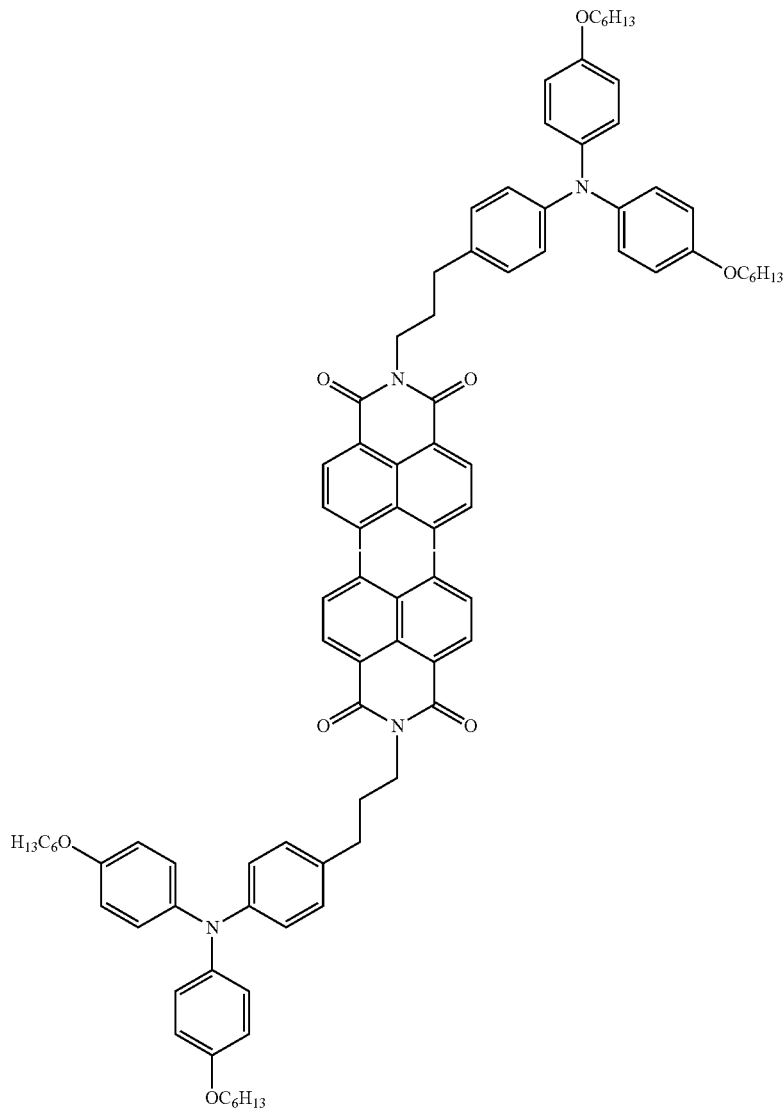

1.18 g (3.00 mmol) of perylenetetracarboxylic dianhydride and 3.17 g (6.30 mmol) of 4-(3-aminopropyl)-N,N-di(4-n-hexyloxyphenyl)aniline were, respectively, suspended and dissolved in 30 ml of N-methylpyrrolidinone and heated at 120° C. for 5 hours. After cooling to room temperature, 60 ml of methanol were added. The precipitate was filtered off with suction, washed with methanol and water, and dried (4.00 g). The crude product was purified by chromatography on silica gel (60 Å, 60-200 µm) with cyclohexane-ethyl acetate-n-propanol (14:3:3). 2.11 g (53% of theory) of dark red solid were obtained with a m.p. of 221-223° C.

UV/vis (methylene chloride): $\lambda_{max}$ ($\epsilon$)=524 nm (74930)
$C_{90}H_{96}N_4O_8$ (M=1361.79 g/mol):

| | | | | | | | |
|---|---|---|---|---|---|---|---|
| calc. | C | 79.38 | H | 7.11 | N | 4.11 | O | 9.40 |
| found | C | 79.4 | H | 7.3 | N | 4.0 | O | 9.2 |

Example 31

Preparation of N,N'-bis{3-[4-(N,N-di-n-hexylphenylamino)phenyl]propyl}-1,7-dicyanoperylenebis(dicarboximide)

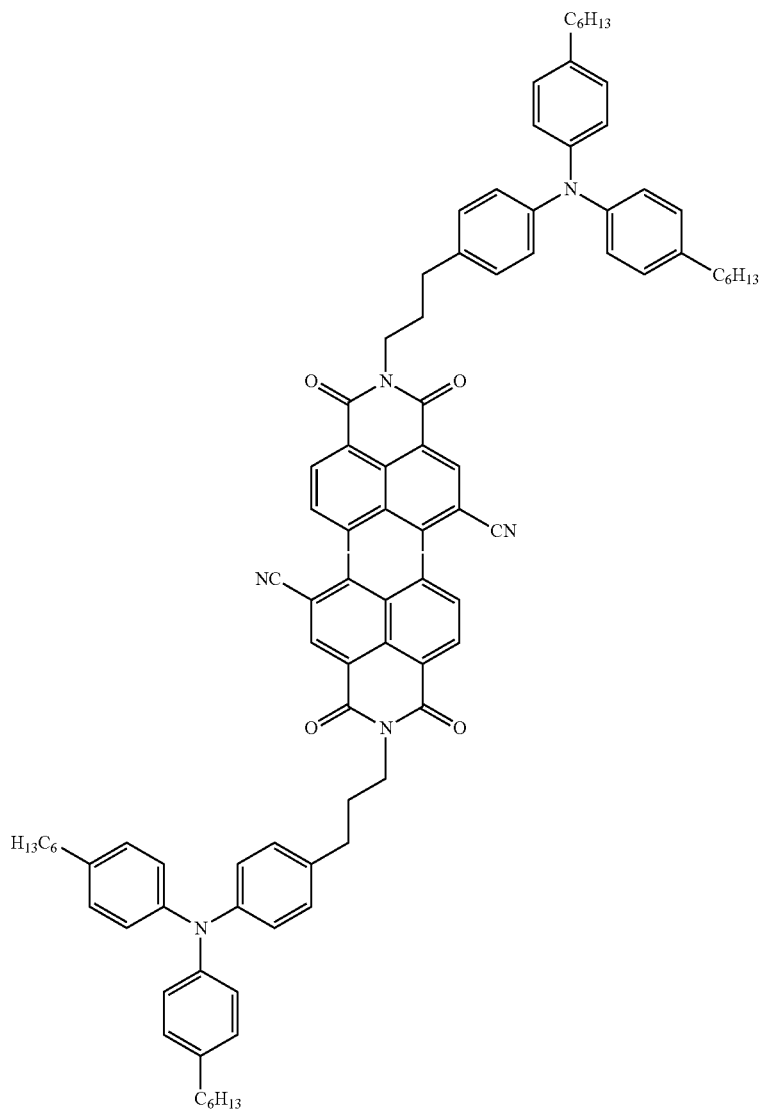

A solution of 2.00 g (1.37 mmol) of N,N'-bis{3-[4-(N,N-di-n-hexylphenylamino)phenyl]-propyl}-1,7-dibromoperylenebis(dicarboximide) in 50 ml of N-methylpyrrolidinone was admixed with 0.37 g (4.1 mmol) of copper cyanide and heated to 150° C. After stirring at this temperature for two hours, the reaction mixture was allowed to cool to room temperature. After the addition of 50 ml of methanol, the reaction mixture was stirred briefly and then filtered. The residue was washed with 30 ml of methanol, then slurried with 10 ml of saturated sodium hydrogencarbonate solution, filtered with suction, washed with water and then with methanol, and dried (1.81 g). The crude product was dissolved in methylene chloride, applied to 10 g of silica gel (60 Å, 60-200 µm) and purified by chromatography on silica gel with toluene-ethyl acetate. 1.69 g of dark red resin were obtained, which were dissolved in 20 ml of nitroethane at reflux temperature and crystallized out in the course of cooling. The solid was filtered off with suction and recrystallized from 100 ml of methyl ethyl ketone. 0.71 g (38% of theory) of dark red microcrystals was obtained, which melted at 204-205° C. According to $^1$H NMR, the substance comprised the 1,6-dicyano isomer as a by-product.

UV/vis (methylene chloride): $\lambda_{max}$ ($\epsilon$)=524 nm (61700)

$C_{92}H_{94}N_6O_4$ (M=1347.81 g/mol):

| | | | | | | | | |
|---|---|---|---|---|---|---|---|---|
| calc. | C | 81.99 | H | 7.03 | N | 6.24 | O | 4.75 |
| found | C | 81.9 | H | 6.9 | N | 6.1 | O | 4.8 |

Example 32

Preparation of N,N'-bis{3-[4-(N,N-di-n-hexyloxyphenylamino)phenyl]-propyl}-1,7-dicyanoperylenebis(dicarboximide)

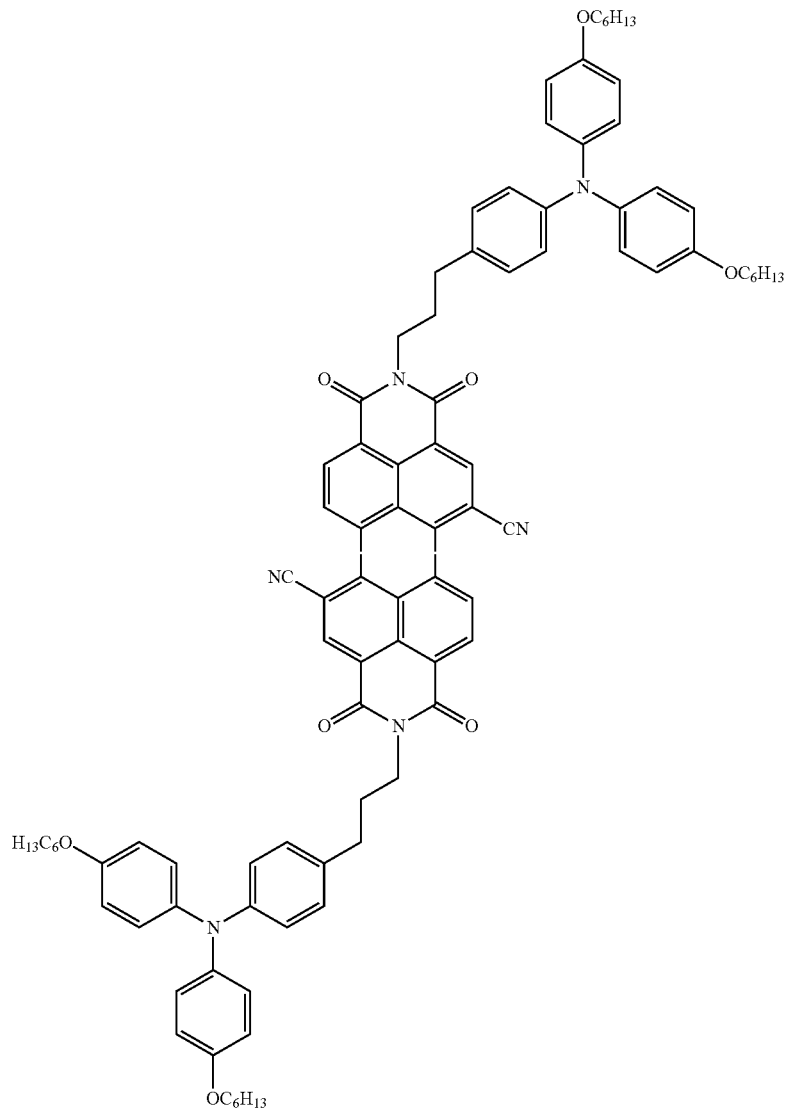

A solution of 2.00 g (1.32 mmol) of N,N'-bis{3-[4-(N,N-di-n-hexyloxyphenylamino)-phenyl]propyl}-1,7-dibromoperylenebis(dicarboximide) in 20 ml of N-methylpyrrolidinone was admixed with 0.35 g (4.0 mmol) of copper cyanide and heated to 150° C. After stirring at this temperature for two hours, the reaction mixture was allowed to cool to room temperature. After the addition of 50 ml of methanol, the reaction mixture was stirred briefly and then filtered. The residue was slurried with 20 ml of saturated sodium hydrogencarbonate solution, filtered with suction, washed with water and then with methanol, and dried (1.78 g). The crude product was chromatographed on alumina (activated, neutral, Brockmann Grade I, 58 Å) with 5:1 methylene chloride-n-heptane. The prepurified product was purified by chromatography on silica gel (60 Å, 60-200 µm) with 6:1:0.1 toluene-n-heptane-acetone. 1.06 g (57% of theory) of dark red microcrystals were obtained, which melted at 206-207° C. According to $^1$H NMR, the substance comprised the 1,6-dicyano isomer as a by-product.

UV/vis (methylene chloride): $\lambda_{max}$ ($\epsilon$)=524 nm (60680)

$C_{92}H_{94}N_6O_8$ (M=1411.81 g/mol):

| | | | | | | | | |
|---|---|---|---|---|---|---|---|---|
| calc. | C | 78.27 | H | 6.71 | N | 5.95 | O | 9.07 |
| found | C | 78.3 | H | 7.0 | N | 5.8 | O | 9.0 |

Example 33

Preparation of N,N'-bis(2-dibutylaminoethyl)-1,7-dibromoperylene-3,4:9,10-bis(dicarboximide)

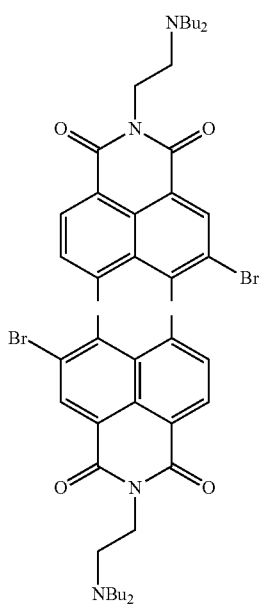

A suspension of 3.60 g (6.54 mmol) of dibromoperylene-3,4:9,10-bis(dicarboxylic-anhydride) (approx. 80%, 1,7-dibromo and approx. 20% 1,6-dibromo isomer) and 2.40 g (13.9 mmol) of 2-dibutylaminoethylamine in 60 ml of chlorobenzene was heated to 80° C. and stirred at this temperature for 4 hours. After cooling to room temperature, solids were filtered off with suction, taken up with 50 ml of methanol and stirred for 3 hours. The solids were filtered off with suction, washed with 30 ml of methanol and dried. The crude product (4.98 g) was recrystallized in dimethylformamide. The precipitate was filtered off, washed with methanol and dried. 4.55 g (81% of theory) of red powder were obtained, which melted at 194° C.

UV/vis (methylene chloride): $\lambda_{max}$ ($\epsilon$)=524 nm (49320)

$C_{44}H_{50}Br_2N_4O_4$ (M=858.72 g/mol):

| calc. | C | 61.54 | H | 5.87 | Br | 18.61 | N | 6.52 | O | 7.45 |
|---|---|---|---|---|---|---|---|---|---|---|
| found | C | 61.2 | H | 5.9 | Br | 18.6 | N | 6.5 | O | 7.8 |

Example 34

Preparation of N,N'-bis(2-dibutylaminopropyl)-1,7-dibromoperylene-3,4:9,10-bis(dicarboximide)

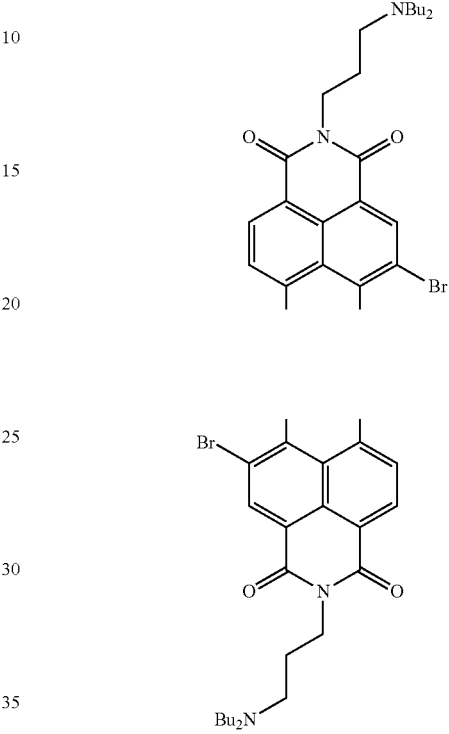

A suspension of 3.50 g (6.36 mmol) of dibromoperylene-3,4:9,10-bis(dicarboxylic-anhydride) (approx. 80% 1,7-dibromo and approx. 20% 1,6-dibromo isomer) and 2.49 g (13.4 mmol) of 3-dibutylaminopropylamine in 60 ml of chlorobenzene was heated to 80° C. and stirred at this temperature for 5.5 hours. After cooling to room temperature, solids were filtered off with suction, taken up with 40 ml of methanol and stirred for 3 hours. The solids were filtered off with suction, washed with 30 ml of methanol and dried. The crude product (4.86 g) was recrystallized in dimethylformamide. The precipitate was filtered off, washed with methanol and dried. 4.33 g (77% of theory) of red powder were obtained, which melted at 179-180° C.

UV/vis (methylene chloride): $\lambda_{max}$ ($\epsilon$)=524 nm (50250)

$C_{46}H_{54}Br_2N_4O_4$ (M=886.78 g/mol):

| calc. | C | 62.31 | H | 6.14 | Br | 18.02 | N | 6.32 | O | 7.22 |
|---|---|---|---|---|---|---|---|---|---|---|
| found | C | 62.1 | H | 6.1 | Br | 18.1 | N | 6.3 | O | 7.4 |

Example 35

Preparation of N,N'-bis(2-dibutylaminopropyl)-1,7-diphenoxyperylene-3,4:9,10-bis(dicarboximide)

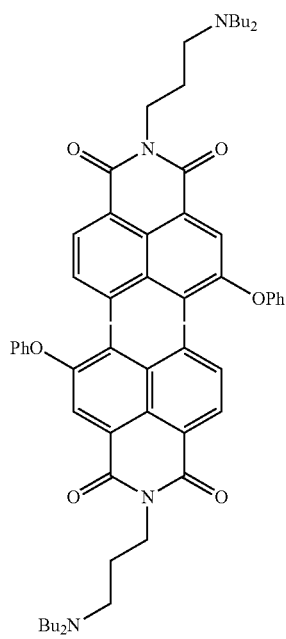

2.00 g (2.26 mmol) of N,N'-bis(2-dibutylaminopropyl)-1,7-dibromoperylene-3,4:9,10-bis(dicarboximide), 0.43 g (4.5 mmol) of phenol and 0.62 g (4.5 mmol) of potassium carbonate were heated in 40 ml of 1-methyl-2-pyrrolidone to 100-105° C. and stirred at this temperature for 6 hours. After cooling, 50 ml of methanol were added and the mixture was stirred for a further 30 min. The precipitate was filtered off with suction, washed with methanol and dried. The crude product (1.84 g) was purified by chromatography on silica gel (60 Å, 60-200 μm) with 6:1:0.02 methylene chloride-methanol-acetone. 1.34 g (65% of theory) of dark red solid were obtained.

UV/vis (methylene chloride): $\lambda_{max}$ ($\epsilon$)=536 nm (49160)
$C_{58}H_{64}N_4O_6$ (M=913.18 g/mol):

| | | | | | | | | |
|---|---|---|---|---|---|---|---|---|
| calc. | C | 76.29 | H | 7.06 | N | 6.14 | O | 10.51 |
| found | C | 75.7 | H | 7.1 | N | 6.3 | O | 10.9 |

Example 36

Preparation of N,N'-bis(2,6-diisopropylphenyl)-1,7-bis{3-[4-(bis-{4-n-hexylphenyl}amino)phenyl]propanethio}perylene-3,4:9,10-bis(dicarboximide)

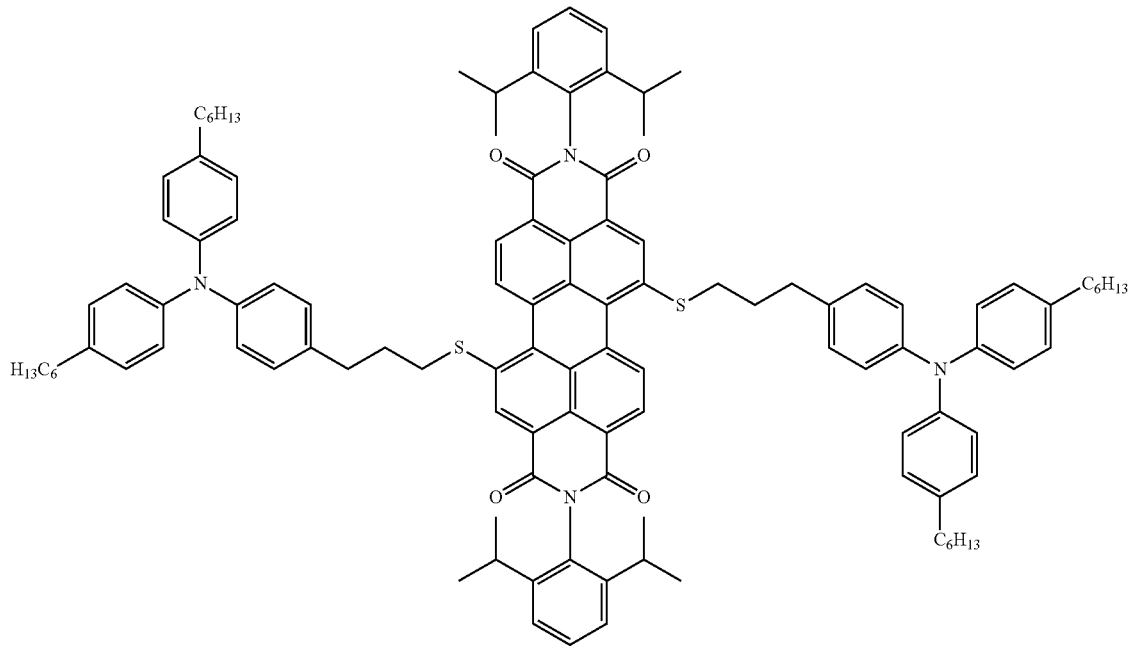

2.00 g (2.30 mmol) of N,N'-bis(2,6-diisopropylphenyl)-1,7(6)-dibromoperylene-3,4:9,10-bis(dicarboximide), 2.58 g (5.30 mmol) of 3-[N,N-(di-4-hexylphenyl)-4-anilino]propane-thiol and 0.74 g (5.3 mmol) of potassium carbonate were stirred in 30 ml of N-methyl-2-pyrrolidone at 80° C. for 7.5 hours. After cooling to room temperature, 50 ml of methanol and water were added. The precipitate was filtered off, washed with methanol and water, and dried. The crude product (2.95 g) was purified by chromatography on silica gel (60 Å, 60-200 μm). The 1st fraction (1.34 g) was recrystallized in 120 ml of isopropanol. 0.53 g (14% of theory) of dark red microcrystals were obtained.

UV/vis (methylene chloride): $\lambda_{max}$ ($\epsilon$)=570 nm (31460)

$C_{114}H_{128}N_4O_4S_s$ (M=1682.44 g/mol):

| | | | | | | | | | |
|---|---|---|---|---|---|---|---|---|---|
| calc. | C | 81.39 | H | 7.67 | N | 3.33 | O | 3.80 | S | 3.81 |
| found | C | 81.5 | H | 7.6 | N | 3.3 | O | 3.8 | S | 3.7 |

Example 37

Preparation of N,N'-bis(2,6-diisopropylphenyl)-1,7-bis{3-[4-(bis-{4-n-hexylphenyl}amino)phenyl]propanesulfonyl}perylene-3,4:9,10-bis(dicarboximide)

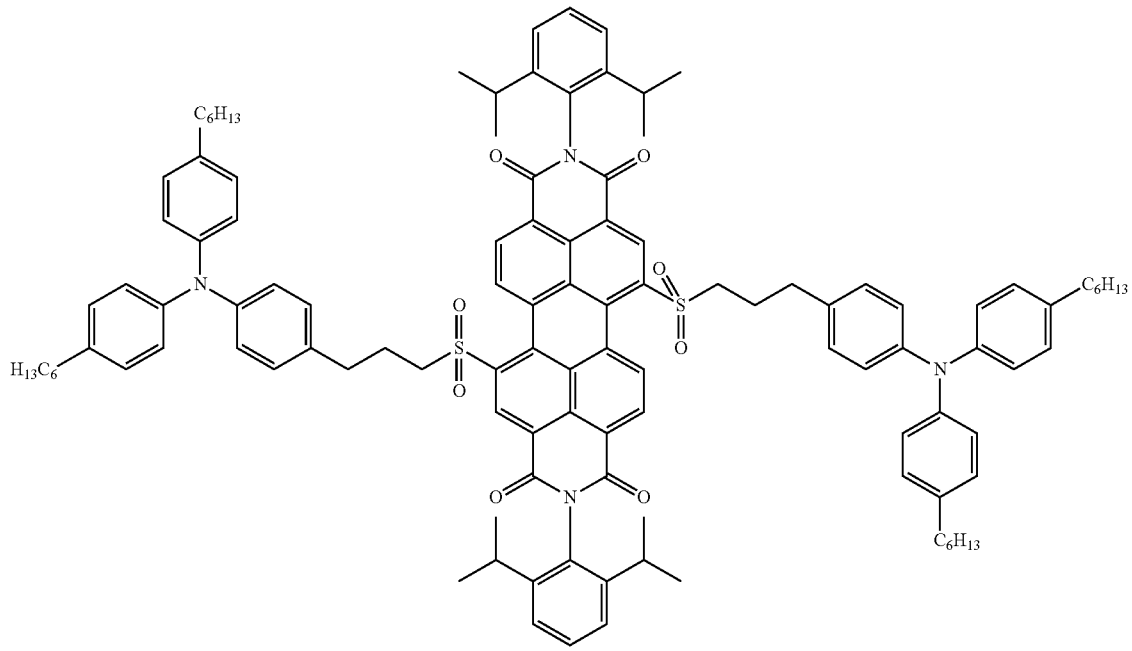

To a solution of 1.00 g (0.59 mmol) of N,N'-bis(2,6-diisopropylphenyl)-1,7-bis{3-[4-(bis-{4-n-hexylphenyl}amino)phenyl]propanethio}perylene-3,4:9,10-bis(dicarboximide) in 20 ml of methylene chloride was added dropwise, at 0° C., 0.93 g (4.2 mmol) of 77% 3-chloroperbenzoic acid. After stirring at 0° C. for one hour, the solution was allowed to warm up to room temperature and stirred for a further 16 hours. After adding 0.18 g (1.19 mmol) of sodium iodide, the solution was stirred at room temperature for 5 hours. The reaction solution was admixed with water. The organic phase was removed, dried over magnesium sulfate and concentrated to dryness. The crude product (1.67 g) was purified by chromatography on silica gel (60 Å, 60-200 μm) with 20:1 methylene chloride-isopropanol. 0.50 g (49% of theory) of dark red solid was obtained.

UV/vis (Methylenchlorid): $\lambda_{max}$ ($\epsilon$)=526 nm (32320)
$C_{114}H_{128}N_4O_8S_s$ (M=1746.44 g/mol):

| | | | | | | | | | |
|---|---|---|---|---|---|---|---|---|---|
| calc. | C | 78.40 | H | 7.39 | N | 3.21 | O | 7.33 | S | 3.67 |
| found | C | 78.3 | H | 7.6 | N | 3.2 | O | 6.6 | S | 3.4 |

Example 38

Preparation of N,N'-bis{3-[4-(N,N-di-n-hexyloxyphenylamino)phenyl]-propyl}naphthalene-1,8:4,5-bis(dicarboximide)

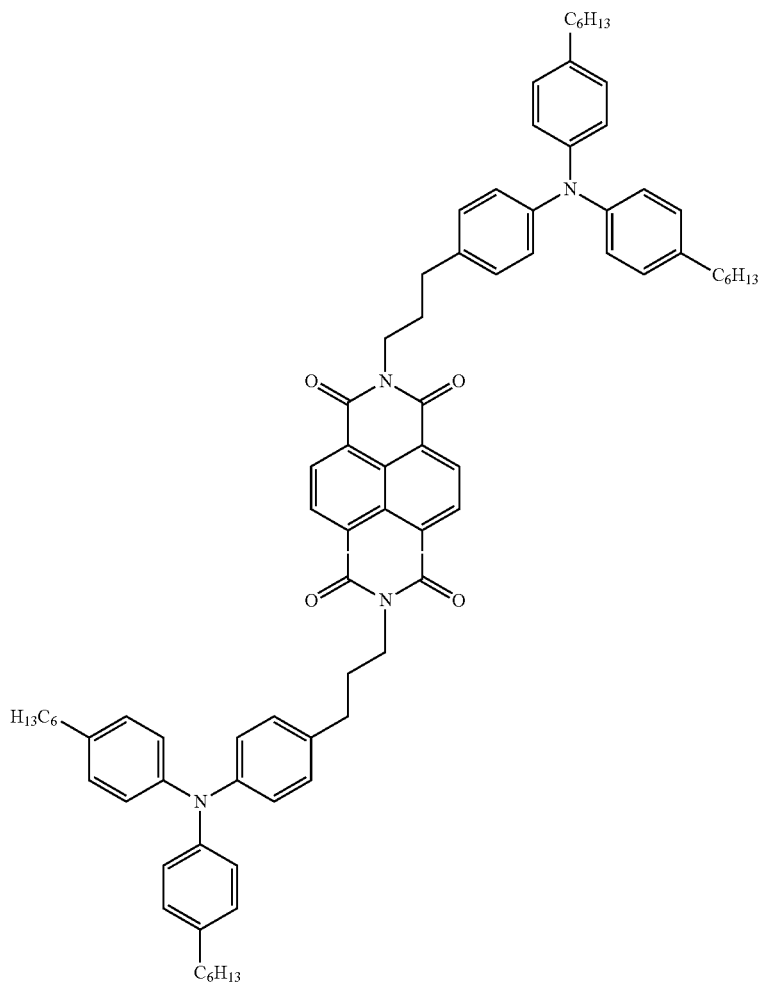

A solution of 1.05 g (3.73 mmol) of 95% 1,4,5,8-naphthalenetetracarboxylic dianhydride and 4.14 g (7.83 mmol) of 4-(3-aminopropyl)-N,N-di-(4-n-hexyloxyphenyl)aniline (see Example 12d)) in 50 ml of toluene was stirred at 80° C. for 10 hours. After cooling to room temperature, the reaction mixture was concentrated to dryness (green-blue oil). The crude product (6.5 g) was purified by chromatography twice on silica gel (60 Å, 60-200 µm) with methylene chloride/n-heptane (5:1) as the eluent. 2.1 g (45% of theory) of pale blue solid were obtained, which melted at 155° C.

UV/vis (methylene chloride): $\lambda_{max}$ ($\epsilon$)=380 nm (29030)

$C_{80}H_{92}N_4O_6$ (M=1237.65 g/mol):

| calc. | C | 77.64 | H | 7.49 | N | 4.53 | O | 10.34 |
| --- | --- | --- | --- | --- | --- | --- | --- | --- |
| found | C | 77.7 | H | 7.4 | N | 4.6 | O | 10.7 |

Example 39

For Preparation cf. Bonnet et al., Synthetic Metals 156 (2006) 1292-1298

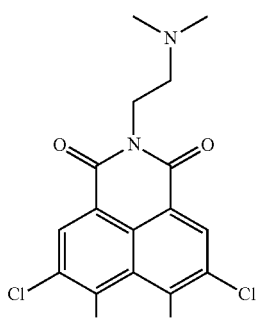

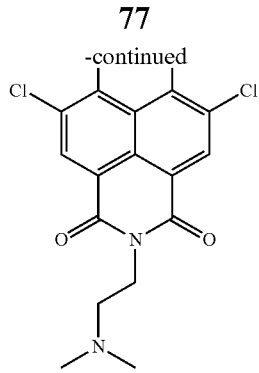

N,N'-Bis(3-dimethylaminoethyl)-1,6,7,12-tetrachloroperylenetetracarboximide was dissolved in NMP in a concentration of $2.97*10^{-3}$ mol/l. The molar extinction coefficient of the compound in NMP was 36930 (1/mol*cm). A portion of this solution was illuminated through a light guide with a 75 watt Xe lamp, such that the entire volume of the solution was covered by the light beam. Simultaneously with the illumination, a UV-VIS spectrometer in transmission mode was used to measure the spectral change.

A band develops at 756 nm, whose intensity increases by 2.7 extinction units within 6 seconds of illumination time.

| Time (sec) | Increase at 756 nm |
|---|---|
| 0 | 0 |
| 2 | 1.0555538 |
| 4 | 2.7220225 |
| 6 | 2.7336044 |

Example 40

N,N'-Bis(3-dimethylaminoethyl)-1,6,7,12-tetrachloroperylenetetracarboximide was applied by vapor deposition to glass with a layer thickness of 130 nm. The dye layer was illuminated through a light guide with a 75 watt Xe lamp. Illumination gives rise to a band at 765 nm.

| Time (min) | 765 nm |
|---|---|
| 0 | 0 |
| 2 | 0.0387932 |

The absorption at 765 nm which develops in the course of illumination regresses to the start value after 15 minutes of storage in the dark.

| Dark storage (min) | 765 nm |
|---|---|
| 0 min dark | 0.0387932 |
| 5 min dark | 0.0186532 |
| 10 min dark | 0.0106751 |
| 15 min dark | 0.0065114 |

Example 41

N,N'-Bis[3-(3,6-di-n-hexyl-N-carbazolyl)propyl]perylenetetracarboximide was dissolved in NMP with a concentration of $8.77*10^{-4}$ mol/l. The molar extinction coefficient of the compound in NMP is 74100 (1/mol*cm). A portion of this solution was illuminated in a 1 mm cuvette with a 75 watt Xe lamp such that the entire volume of the solution was covered by the incident light beam. Simultaneously with the illumination, a UV-VIS spectrometer in transmission mode was used to measure the spectral change through an Ulbricht sphere.

A band develops at 706 nm, which rises within 2 minutes of illumination to >80% of its value in the case of infinite illumination time, and, after subsequent storage in the dark, declines by half (recovery).

| Illumination: | | Storage in the dark: | |
|---|---|---|---|
| Time (min) | Increase at 706 nm | Time (min) | Recovery at 706 nm |
| 0 | 0 | 30 | 0.0250429 |
| 2 | 0.0499492 | | |

Example 42

Performance of paper dyeing with N,N'-bis(3-dimethylaminoethyl)-1,6,7,12-tetrachloroperylenetetracarboximide The pulp (wood-free cellulose pulp) was weighed in. The moist pulp, corresponding to 1.7 g of dry mass, was added to 65 ml of water and the material was stirred for 10-15 min. 0.1 g of N,N'-bis(3-dimethylaminoethyl)-1,6,7,12-tetrachloroperylenetetracarboximide was dissolved in water and 2 ml of acetic acid and made up to 100 ml. 10 ml of this solution were added to the prepared pulp, and the mixture was made up to 1 liter with water. The mixture was filtered with suction through a filter. The pulp was removed from the filter and dried between two filter papers at 90° C. for 5 min.

The dried sample is illuminated with a 75 watt xenon lamp through a Y light guide and the resulting UV absorption is measured with a UV-VIS spectrometer simultaneously with the illumination.

The absorption at 768 nm which develops on illumination regresses by 86% (of the value which developed after 2 minutes of illumination) after storage in the dark for 30 minutes.

| Time (min) | 768 nm | | 768 nm |
|---|---|---|---|
| 0 | 0 | After 30 min of dark storage | 0.0538442 |
| 2 | 0.3915774 | | |

Example 43

Performance of "Dripping Tests" and Subsequent Illumination on Paper 0.1 g of N,N'-bis(3-dimethylaminoethyl)-1,6,7,12-tetrachloroperylenetetracarboximide were dissolved in water and 2 ml of acetic acid and made up to 100 ml. A pipette was used to take up 2 ml of solution. This solution was dripped onto a sheet of paper and dried at 90° C.

The dried sample was illuminated with a 75 watt xenon lamp through a Y light guide and the resulting UV absorption was measured with a UV-VIS spectrometer simultaneously with the illumination.

The absorption at 768 nm which develops on illumination regresses to approx. 11% of the starting value after storage in the dark for 30 minutes.

|  | E max at 770 nm |
| --- | --- |
| Start of illumination | 0 |
| 38 sec. of illumination | 0.4982 |
| 30 min in the dark | 0.0526 |

The invention claimed is:

1. A process for altering the absorption of electromagnetic radiation of at least one compound represented by formulae (I)

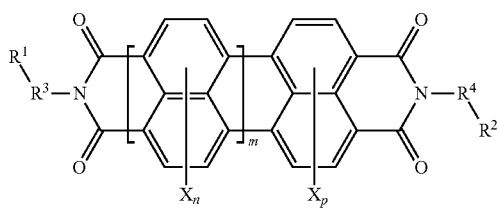

which comprises
irradiating the at least one compound with electromagnetic radiation at a wavelength from 300 to 750 nm wherein
the irradiation with electromagnetic radiation at a wavelength from 300 to 750 nm results in a non-permanent bathochromic shift in the absorption spectrum of the at least one compound represented by formula (I)
wherein
$R^1$, $R^2$ are the same or different and are each independently amino, $C_1$-$C_8$-alkylamino, $C_1$-$C_8$-dialkylamino, arylamino, diarylamino, N-heterocyclyl, triarylaminyl, hydroxyl, $C_1$-$C_8$-alkoxy, aryloxy,
$R^3$, $R^4$ are the same or different and are each independently a single bond, $C_1$-$C_8$-alkylene, $C_3$-$C_6$-cycloalkylene, arylene, $C_8$-$C_{14}$-phenylalkylene,
X are the same or different and are each independently $C_1$-$C_{20}$-alkoxy, $C_1$-$C_{20}$-alkylthio, aryloxy, arylthio, halogen, cyano, CO—$_2$R, SO$_3$R, SO$_2$R, or a group

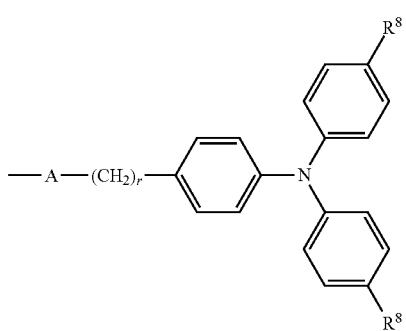

where
A is S, SO$_2$,
r is 2, 3, 4, 5, 6,
$R^8$ is $C_1$-$C_{20}$-alkyl, $C_1$-$C_{20}$-alkoxy,
and
if m=1, different X together may be a thio group,
R are the same or different and are each independently H, $C_1$-$C_8$-alkyl, aryl,
n, p is 0, 1, 2, 3 or 4,
m is 0, 1, or 2,
and where the substituents R, $R^1$, $R^2$, $R^3$ or $R^4$ may each be interrupted at any position by one or more heteroatoms with valences saturated if appropriate by H, where the number of these heteroatoms is not more than four, and/or may be substituted in each case at any position, but not more than five times, by NR$^5$R$^6$, CONR$^5$R$^6$, COOM, COOR$^5$, SO$_3$M, SO$_3$R$^5$, where
$R^5$, $R^6$ are the same or different and are each independently H, $C_1$-$C_8$-alkyl, aryl,
M is H, alkali metal, NR$^7_4$,
$R^7$ is independently H, $C_1$-$C_8$-alkyl,
CN, NO$_2$, $C_1$-$C_{20}$-alkyl, $C_1$-$C_{20}$-alkoxy, aryl, aryloxy, heterocycles, heteroatoms or halogen, where these may likewise be substituted not more than twice by the groups mentioned.

2. The process according to claim 1, wherein
$R^1$, $R^2$ are the same or different and are each independently amino, $C_1$-$C_8$-alkylamino, $C_1$-$C_8$-dialkylamino, arylamino, diarylamino, N-heterocyclyl, N,N-diarylanilin-4-yl,
$R^3$, $R^4$ are the same or different and are each independently a single bond, $C_1$-$C_8$-alkylene,
X are the same or different and are each independently $C_1$-$C_{20}$-alkoxy, aryloxy, halogen, cyano, SO$_2$R, or a group

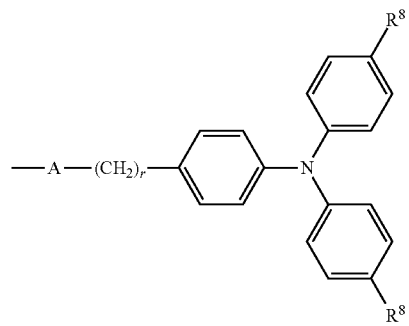

where
A is S, SO$_2$,
r is 2, 3, 4, 5, 6,
$R^8$ is $C_1$-$C_{20}$-alkyl, $C_1$-$C_{20}$-alkoxy,
m is 1 or 2,
and where the substituents $R^1$, $R^2$, $R^3$ and $R^4$ may each be substituted at any position according to claim 1 or interrupted by heteroatoms.

3. The process according to claim 1, wherein
$R^1$, $R^2$ are both amino, $C_1$-$C_8$-alkylamino, $C_1$-$C_8$-dialkylamino, arylamino, diarylamino, N-heterocyclyl, N,N-diarylanilin-4-yl,
$R^3$, $R^4$ are the same or different and are each independently a single bond, $C_1$-$C_8$-alkylene, X are the same or different and are each independently halogen, cyano, aryloxy, or a group

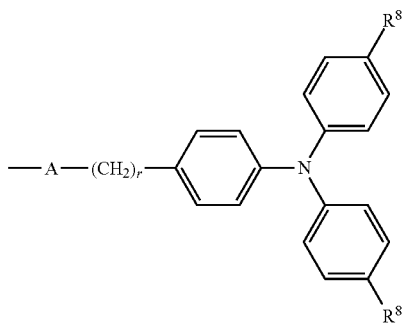

where
A is S, $SO_2$,
r is 2, 3, 4, 5, 6,
$R^8$ is $C_1$-$C_{20}$-Alkyl, $C_1$-$C_{20}$-Alkoxy,
m is 1 or 2,
and where the substituents $R^1$, $R^2$, $R^3$ and $R^4$ may each be substituted at any position according to claim 1 or interrupted by heteroatoms.

4. The process according to claim 1, wherein the irradiation with electromagnetic radiation at a wavelength from 300 to 750 nm results in a visually perceptible color change by the at least one compound represented by formula (I).

5. The process according to claim 1, wherein the irradiation with electromagnetic radiation at a wavelength from 300 to 750 nm results in an absorption by the at least one compound represented by formula (I) in the IR.

* * * * *